US012760011B2

(12) United States Patent
Kawamoto et al.

(10) Patent No.: US 12,760,011 B2
(45) Date of Patent: Oct. 13, 2026

(54) DISULFIDE COMPOUND, POLYSULFIDE COMPOUND, AND USE THEREOF

(71) Applicant: KUMIAI CHEMICAL INDUSTRY CO., LTD., Tokyo (JP)

(72) Inventors: Kei Kawamoto, Tokyo (JP); Seisuke Ito, Tokyo (JP)

(73) Assignee: KUMIAI CHEMICAL INDUSTRY CO., LTD., Tokyo (JP)

(*) Notice: Subject to any disclaimer, the term of this patent is extended or adjusted under 35 U.S.C. 154(b) by 408 days.

(21) Appl. No.: 18/695,101

(22) PCT Filed: Oct. 28, 2022

(86) PCT No.: PCT/JP2022/040287

§ 371 (c)(1),
(2) Date: Mar. 25, 2024

(87) PCT Pub. No.: WO2023/074828

PCT Pub. Date: May 4, 2023

(65) Prior Publication Data

US 2024/0391909 A1 Nov. 28, 2024

(30) Foreign Application Priority Data

Oct. 29, 2021 (JP) ................................ 2021-177271

(51) Int. Cl.
*C07D 413/12* (2006.01)
*C07D 403/12* (2006.01)

(52) U.S. Cl.
CPC ......... *C07D 413/12* (2013.01); *C07D 403/12* (2013.01)

(58) Field of Classification Search
CPC ....... C07D 413/12; C07D 231/20; A01P 7/04; A01P 13/00; A01N 43/56
See application file for complete search history.

(56) References Cited

U.S. PATENT DOCUMENTS

| | | | | |
|---|---|---|---|---|
| 3,350,407 A * | 10/1967 | Fletcher | C07D 233/56 548/365.1 |
| 7,238,689 B2 | 7/2007 | Nakatani et al. | |
| 7,256,298 B2 | 8/2007 | Nakatani et al. | |
| 7,488,831 B2 | 2/2009 | Uchida | |
| 2004/0110749 A1 | 6/2004 | Nakatani et al. | |
| 2005/0215797 A1 | 9/2005 | Nakatani et al. | |
| 2007/0185334 A1 | 8/2007 | Uchida | |
| 2007/0249844 A1 | 10/2007 | Nakatani et al. | |
| 2010/0004128 A1 | 1/2010 | Boehmer et al. | |
| 2023/0012374 A1* | 1/2023 | Uchida | A01P 13/00 |

FOREIGN PATENT DOCUMENTS

| | | | | |
|---|---|---|---|---|
| JP | 08-208620 | | 8/1996 | |
| WO | WO 2005/105755 | | 11/2005 | |
| WO | WO-2007096576 | A1 * | 8/2007 | C07D 261/04 |
| WO | WO 2022/138781 | | 6/2022 | |
| WO | WO 2022/191292 | | 9/2022 | |

OTHER PUBLICATIONS

International Search Report for PCT/JP2022/040287 dated Jan. 10, 2023.

Chunhui, et al.; "Synthesis, Crystal Structure, Insecticidal and Acaricidal of Novel N-Bridged Derivatives of 2-(p-Chlorophenyl)pyrrole", Chinese Journal of Organic Chemistry, 2009, vol. 29, No. 6, pp. 929-935.

* cited by examiner

*Primary Examiner* — Scarlett Y Goon
*Assistant Examiner* — Grace Ching Hsu
(74) *Attorney, Agent, or Firm* — Stephen J. Weyer, Esq.; Stites & Harbison, PLLC

(57) ABSTRACT

The present invention provides a compound of formula (2), and use thereof. The compound of formula (2) is useful as a pest control agent. The compound of formula (2) is also useful as a herbicide, particularly as a production intermediate of pyroxasulfone.

(2)

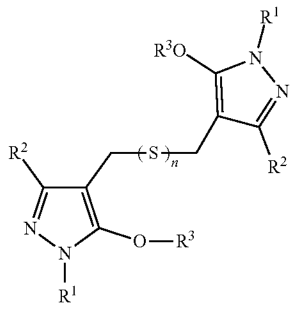

25 Claims, No Drawings

DISULFIDE COMPOUND, POLYSULFIDE COMPOUND, AND USE THEREOF

TECHNICAL FIELD

The present invention relates to a compound of the following formula (2) and use thereof.

(2)

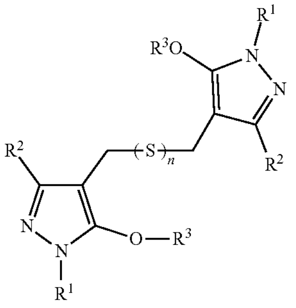

wherein $R^1$, $R^2$, $R^3$ and n are as described herein.

Specifically, the present invention relates to a novel compound of formula (2), and a pest control agent containing the compound of formula (2) as an active ingredient.

The present invention also relates to a process for producing a compound of the following formula (4) and a compound of the following formula (5) using the compound of formula (2). The compound of formula (2) is a useful production intermediate of the compound of formula (4) and the compound of formula (5).

(4)

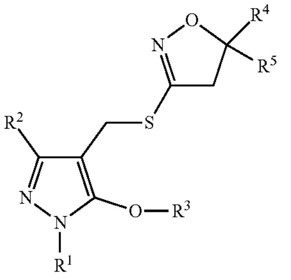

(5)

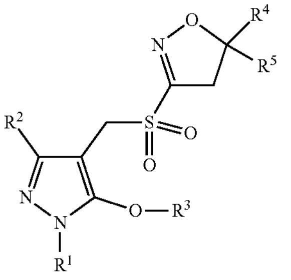

wherein $R^1$, $R^2$, $R^3$, $R^4$ and $R^5$ are as described herein.

BACKGROUND ART

In the fields of agriculture and horticulture, various pest control agents are used. Many of these agents cannot be, however, said to be sufficiently satisfactory. Accordingly, development of a novel pest control agent is always demanded.

U.S. Pat. No. 3,350,407 (Patent Document 6) describes a di[(pyrazol-3-yl)methyl]disulfide compound, but does not mention insecticidal activity thereof.

In addition, this patent document does not disclose a compound of formula (2) of the present invention at all.

Meanwhile, WO 2002/062770 (Patent Document 1) discloses useful herbicides. Among these, pyroxasulfone is well known as a herbicide having excellent herbicidal activity. WO 2004/013106 A1 (Patent Document 2) discloses that a compound of formula (4), particularly a compound of the following formula (4-a), is useful as a production intermediate of pyroxasulfone.

WO 2004/013106 A1 (Patent Document 2) describes a process for producing the compound of formula (4-a). The process described in WO 2004/013106 A1 (Patent Document 2) has, however, a problem in industrial practice. For example, opportunity and process for purifying the intermediate are limited.

Preparation of the compound of formula (4-a) is also disclosed in WO 2005/095352 A1 (Patent Document 3) and WO 2005/105755 A1 (Patent Document 4), which are as follows:

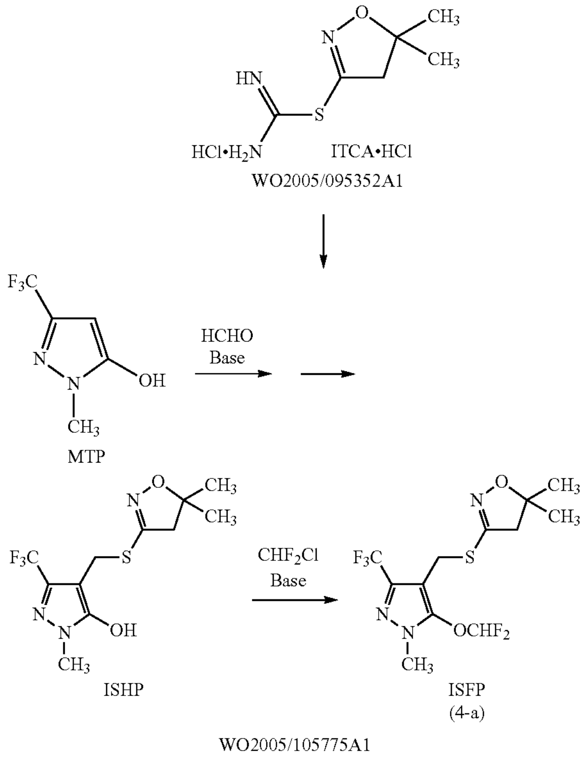

The process described in WO 2005/095352 A1 (Patent Document 3) and WO 2005/105755 A1 (Patent Document 4) is a superior process. On the other hand, there is still room for improvement in this process because a special manufacturing equipment (hermetically closed equipment) is required for the sensitization of the intermediate (ISHP in the above scheme), and as described below.

The process for producing the compound of formula (4-a) described in WO 2021/002484 A9 (Patent Document 5) is a superior process that has solved the problems in the preparation of the compound of formula (4-a) described in Patent Document 3. In production on an industrial scale, however, there is still room for improvement as described below.

Many of sulfur-containing organic compounds have distinctive bad smell in general, and it is necessary to consider control of this bad smell in production on an industrial scale. In addition to such a situation, as for pharmaceutical/agricultural compounds and synthetic intermediates thereof, it is required to produce high quality target compounds in view of activity/safety and stability. When an intermediate compound obtained during production procedures is in a liquid form, there is no choice but to employ distillation as an isolation process and/or purification process for the compound. In performing distillation of a sulfur-containing organic compound on an industrial scale, there is a need for special facilities and complicated operations for preventing spread of bad smell to the environment. When an intermediate compound obtained during production procedures is in a solid form, there is a choice of filtration and/or recrystallization as the isolation process and/or the purification process, and quality improvement and storage stability of the intermediate compound are expected.

CITATION LIST

Patent Document

Patent Document 1: WO 2002/062770 A1
Patent Document 2: WO 2004/013106 A1
Patent Document 3: WO 2005/095352 A1
Patent Document 4: WO 2005/105755 A1
Patent Document 5: WO 2021/002484 A1
Patent Document 6: U.S. Pat. No. 3,350,407

SUMMARY OF INVENTION

Technical Problem

It is an object of the present invention to provide a novel compound having pest control activity.

It is another object of the present invention to provide a process for producing a compound of formula (4) with which the compound of formula (4) can be safely produced for providing a novel industrially preferable production process and an intermediate thereof.

It is still another object of the present invention to provide a novel intermediate compound having high crystallinity with which a choice of filtration and/or recrystallization is provided as an isolation process and/or a purification process.

Solution to Problem

In consideration of the above-described situations, the present inventors made earnest studies. As a result, it was found that the above-described problem can be solved unexpectedly by providing a compound of formula (2) and use thereof. Based on this finding, the present inventors have accomplished the present invention. Specifically, the present invention provides the following:

[1] A compound of formula (2), or a mixture thereof:

(2)

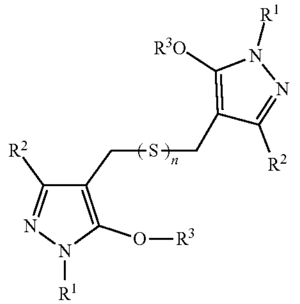

wherein $R^1$, $R^2$ and $R^3$ are each independently a (C1-C6) alkyl optionally substituted with one or more substituents, and n is an integer of 2 or more.

[2] The compound or a mixture thereof according to [1], wherein $R^1$ is a (C1-C4)alkyl, $R^2$ is a (C1-C4)perfluoroalkyl, $R^3$ is a (C1-C4)alkyl optionally substituted with 1 to 9 fluorine atoms, and n is an integer of 2 to 5 (preferably, n is 2 or 3).

[3] The compound according to [1], wherein $R^1$ is methyl, $R^2$ is trifluoromethyl, $R^3$ is a difluoromethyl, and n is 2.

[4] A pest control agent comprising, as an active ingredient, the compound or a mixture thereof according to any one of [1] to [3].

[5] A process for producing a compound of formula (4) comprising the following step ii:

(step ii) a step of reacting a compound of formula (2) with a compound of formula (3) to produce a compound of formula (4):

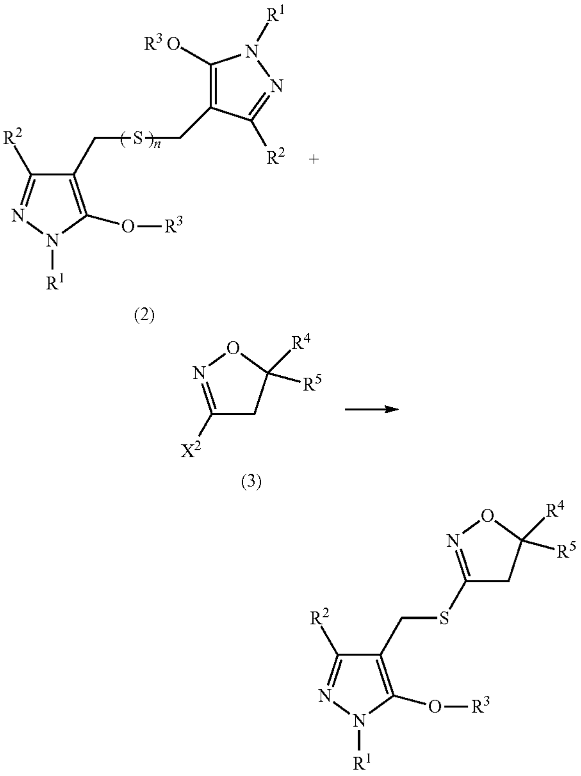

(2) (3) (4)

wherein $R^1$, $R^2$, $R^3$, $R^4$ and $R^5$ are each independently a (C1-C6)alkyl optionally substituted with one or more substituents, $X^2$ is a halogen atom, and n is an integer of 2 or more.

[6] The process according to [5], wherein the reaction in the step ii is performed using a reducing agent.

[7] The process according to [5], wherein the step ii is a step of reacting the compound of formula (2) with the compound of formula (3) with a reducing agent to produce the compound of formula (4):

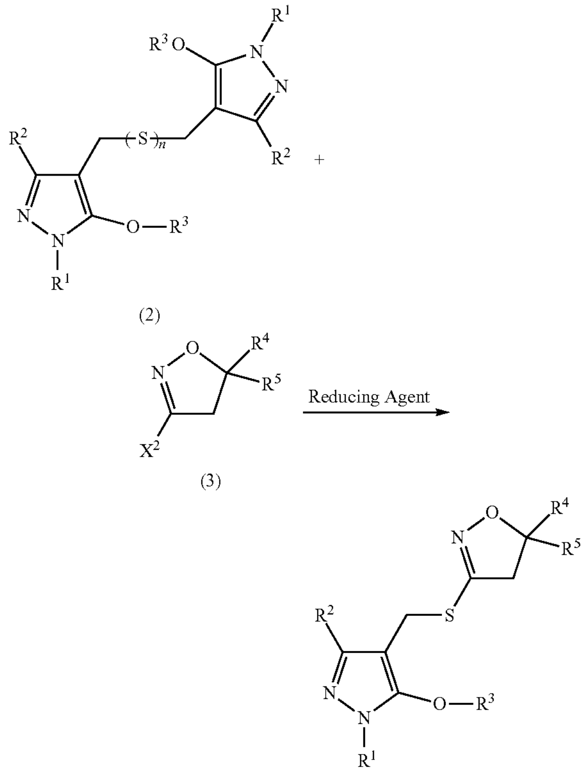

(2) (3) (4)

wherein $R^1$, $R^2$, $R^3$, $R^4$ and $R^5$ are each independently a (C1-C6)alkyl optionally substituted with one or more substituents, $X^2$ is a halogen atom, and n is an integer of 2 or more.

[8] The process according to [5], wherein the step ii is a step of reacting the compound of formula (2) using a reducing agent, and then with the compound of formula (3) in the presence of a base to produce the compound of formula (4).

[9] The process according to [5], wherein the step ii is a step of reacting the compound of formula (2) using a reducing agent in the presence of a base, and then with the compound of formula (3) in the presence of a base to produce the compound of formula (4).

[10] The process according to [5], wherein the step ii is a step of reacting the compound of formula (2) using a reducing agent and an inorganic sulfur compound in the presence of a base, and then with the compound of formula (3) in the presence of a base to produce the compound of formula (4).

[11] The process according to any one of [6] to [10], wherein the reducing agent in the step ii is an alkali metal hydroxymethanesulfinate or a borohydride compound.

[12] The process according to any one of [6] to [10], wherein the reducing agent in the step ii is an alkali metal hydroxymethanesulfinate.

[13] The process according to any one of [6] to [10], wherein the reducing agent in the step ii is a borohydride compound.

[14] The process according to any one of [6] to [10], wherein the reducing agent in the step ii is a sodium hydroxymethanesulfinate dihydrate or sodium borohydride.

[15] The process according to any one of [6] to [10], wherein the reducing agent in the step ii is a sodium hydroxymethanesulfinate dihydrate.

[16] The process according to any one of [6] to [10], wherein the reducing agent in the step ii is sodium borohydride.

[17] The process according to any one of [5] to [7], wherein the reaction in the step ii is performed in the presence of a base.

[18] The process according to [8], [9], [10], or [17], wherein the base in the step ii is an alkali metal carbonate or an alkali metal hydroxide (preferably, when the reducing agent in the step ii is an alkali metal hydroxymethanesulfinate, the base in the step ii is an alkali metal carbonate, and when the reducing agent in the step ii is a borohydride compound, the base in the step ii is an alkali metal hydroxide).

[19] The process according to [8], [9], [10], or [17], wherein the base in the step ii is potassium carbonate or sodium hydroxide (preferably, when the reducing agent in the step ii is a sodium hydroxymethanesulfinate dihydrate, the base in the step ii is potassium carbonate, and when the reducing agent in the step ii is sodium borohydride, the base in the step ii is sodium hydroxide).

[20] The process according to [8], [9], [10], or [17], wherein the base in the step ii is an alkali metal carbonate.

[21] The process according to [8], [9], [10], or [17], wherein the base in the step ii is an alkali metal hydroxide.

[22] The process according to [8], [9], [10], or [17], wherein the base in the step ii is sodium carbonate or potassium carbonate.

[23] The process according to [8], [9], [10], or [17], wherein the base in the step ii is potassium carbonate.

[24] The process according to [8], [9], [10], or [17], wherein the base in the step ii is sodium hydroxide or potassium hydroxide.

[25] The process according to [8], [9], [10], or [17], wherein the base in the step ii is sodium hydroxide.

[26] The process according to any one of [5] to [9] and [11] to [25], wherein the reaction in the step ii is performed using an inorganic sulfur compound.

[27] The process according to [10] or [26], wherein the inorganic sulfur compound in the step ii is sodium sulfide, potassium sulfide, sodium hydrosulfide, potassium hydrosulfide, sodium disulfide, or potassium disulfide.

[28] The process according to [10] or [26], wherein the inorganic sulfur compound in the step ii is sodium hydrosulfide or potassium hydrosulfide.

[29] The process according to [10] or [26], wherein the inorganic sulfur compound in the step ii is sodium hydrosulfide.

[30] The process according to any one of [5] to [29], wherein a reaction temperature in the step ii is 10° C. to 60° C.

[31] The process according to any one of [5] to [29], wherein a reaction temperature in the step ii is 40° C. to 70° C.

[32] The process according to any one of [5] to [31], wherein $R^1$ is a (C1-C4)alkyl, $R^2$ is a (C1-C4)perfluoroalkyl, $R^3$ is a (C1-C4)alkyl optionally substituted with 1 to 9 fluorine atoms, $R^4$ is a (C1-C4)alkyl, $R^5$ is a (C1-C4)alkyl, n is an integer of 2 to 5, and $X^2$ is a chlorine atom or a bromine atom.

[33] The process according to any one of [5] to [31], wherein $R^1$ is methyl, $R^2$ is trifluoromethyl, $R^3$ is difluoromethyl, $R^4$ is methyl, $R^5$ is methyl, n is 2, and $X^2$ is a chlorine atom or a bromine atom.

[34] The process according to any one of [5] to [33], wherein $X^2$ is a chlorine atom.

[35] The process according to any one of [5] to [34], further comprising the following step i before the step ii:

(step i) a step of producing the compound of formula (2) including reacting a compound of formula (1) with a sulfur compound:

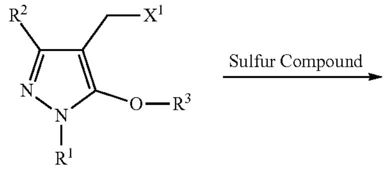

(1)

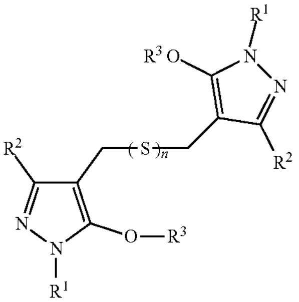

(2)

wherein $R^1$, $R^2$, and $R^3$ are each independently a (C1-C6)alkyl optionally substituted with one or more substituents, $X^1$ is a halogen atom, and n is an integer of 2 or more.

[36] The process according to [35], wherein the step i is the following step (i-a):

(step i-a) a step of reacting the compound of formula (1) with an inorganic sulfur compound and sulfur to produce the compound of formula (2):

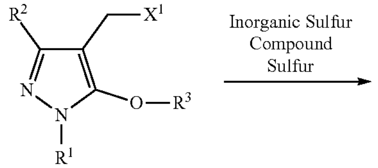

(1)

-continued

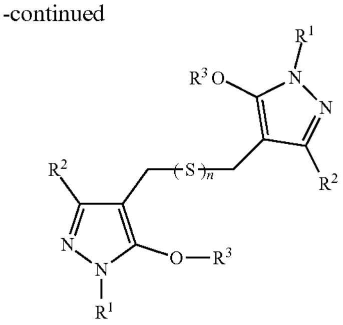

(2)

wherein $R^1$, $R^2$, $R^3$, $X^1$ and n are as defined in [35].

[37] The process according to [35], wherein the sulfur compound in the step i is an inorganic sulfur compound and sulfur.

[38] The process according to [36] or [37], wherein the inorganic sulfur compound in the step i is sodium sulfide.

[39] The process according to [35], wherein the step i is the following step (i-b):

(step i-b) a step of reacting the compound of formula (1) with a sulfur compound (preferably thiourea, a substituted thiourea, a thiocarboxylate, a thioamide, a thiosulfate, or a xanthate salt, more preferably thiourea, N,N-dimethylthioformamide, potassium thioacetate, or sodium thiosulfate, and further preferably thiourea), hydrolyzing the resultant, and reacting the resultant with an oxidizing agent to produce the compound of formula (2):

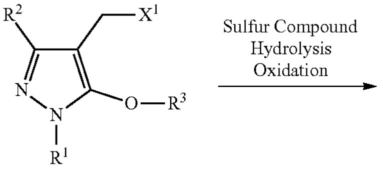

(1)

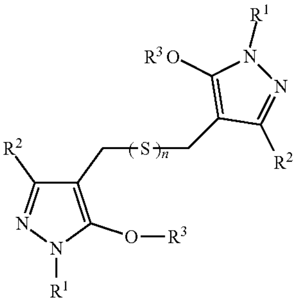

(2)

wherein $R^1$, $R^2$, $R^3$, $X^1$ and n are as defined in [35].

[40] The process according to [35], wherein the sulfur compound in the step i is thiourea, a substituted thiourea, a thiocarboxylate, a thioamide, a thiosulfate, or a xanthate salt, more preferably thiourea, N,N-dimethylthioformamide, potassium thioacetate, or sodium thiosulfate, and further preferably thiourea).

[41] The process according to any one of [35] to [40], wherein $R^1$ is a (C1-C4)alkyl, $R^2$ is a (C1-C4)perfluoroalkyl, $R^3$ is a (C1-C4)alkyl optionally substituted with 1 to 9 fluorine atoms, n is an integer of 2 to 5, and $X^1$ is a chlorine atom or a bromine atom.

[42] The process according to any one of [35] to [40], wherein $R^1$ is methyl, $R^2$ is trifluoromethyl, $R^3$ is difluoromethyl, n is 2, and $X^1$ is a chlorine atom or a bromine atom.

[43] A process for producing a compound of formula (2) comprising the following step i:

(step i) a step of producing the compound of formula (2) including reacting a compound of formula (1) with a sulfur compound:

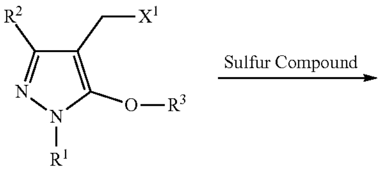

(1)

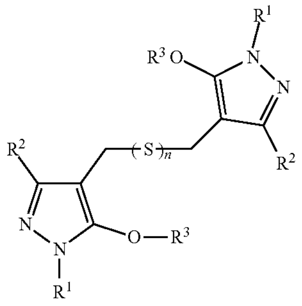

(2)

wherein $R^1$, $R^2$, and $R^3$ are each independently a (C1-C6)alkyl optionally substituted with one or more substituents, $X^1$ is a halogen atom, and n is an integer of 2 or more.

[44] The process according to [43], wherein the step i is the following step (i-a):

(step i-a) a step of reacting the compound of formula (1) with an inorganic sulfur compound and sulfur to produce the compound of formula (2):

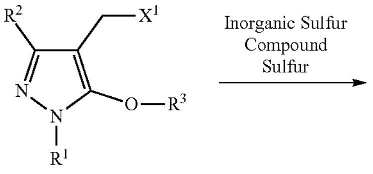

(1)

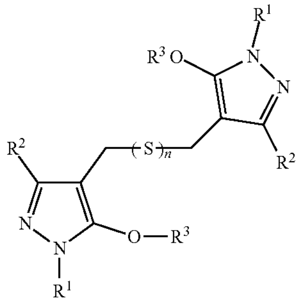

(2)

wherein $R^1$, $R^2$, $R^3$, $X^1$ and n are as defined in [43].

[45] The process according to [43], wherein the sulfur compound in the step i is an inorganic sulfur compound and sulfur.

[46] The process according to [44] or [45], wherein the inorganic sulfur compound in the step i is sodium sulfide.

[47] The process according to [43], wherein the step i is the following step (i-b):

(step i-b) a step of reacting the compound of formula (1) with a sulfur compound (preferably thiourea, a substituted thiourea, a thiocarboxylate, a thioamide, a thiosulfate, or a xanthate salt, more preferably thiourea, N,N-dimethylthioformamide, potassium thioacetate, or sodium thiosulfate, and further preferably thiourea), hydrolyzing the resultant, and reacting the resultant with an oxidizing agent to produce the compound of formula (2):

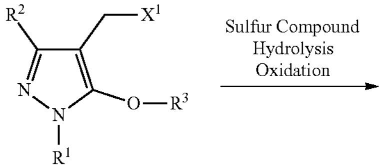

(1)

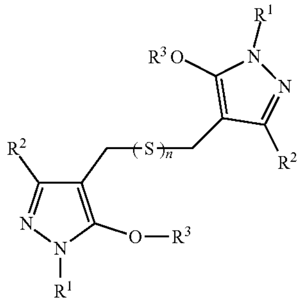

(2)

wherein $R^1$, $R^2$, $R^3$, $X^1$ and n are as defined in [43].

[48] The process according to [43], wherein the sulfur compound in the step i is thiourea, a substituted thiourea, a thiocarboxylate, a thioamide, a thiosulfate, or a xanthate salt, more preferably thiourea, N,N-dimethylthioformamide, potassium thioacetate, or sodium thiosulfate, and further preferably thiourea).

[49] The process according to any one of [43] to [48], wherein $R^1$ is a (C1-C4)alkyl, $R^2$ is a (C1-C4)perfluoroalkyl, $R^3$ is a (C1-C4)alkyl optionally substituted with 1 to 9 fluorine atoms, n is an integer of 2 to 5, and $X^1$ is a chlorine atom or a bromine atom.

[50] The process according to any one of [43] to [48], wherein $R^1$ is methyl, $R^2$ is trifluoromethyl, $R^3$ is difluoromethyl, n is 2, and $X^1$ is a chlorine atom or a bromine atom.

[51] The process according to any one of [43] to [50], wherein $X^1$ is a chlorine atom.

[52] A process for producing a compound of formula (5) comprising:

(step ii) a step of reacting a compound of formula (2) with a compound of formula (3) to produce a compound of formula (4):

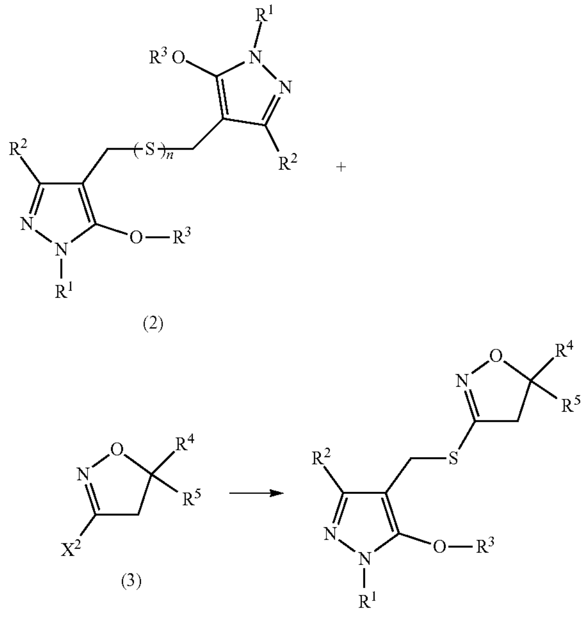

(2)

(3)

(4)

wherein $R^1$, $R^2$, $R^3$, $R^4$ and $R^5$ are each independently a (C1-C6)alkyl optionally substituted with one or more substituents, $X^2$ is a halogen atom, and n is an integer of 2 or more; and (step iii) a step of reacting the compound of formula (4) with an oxidizing agent to produce the compound of formula (5):

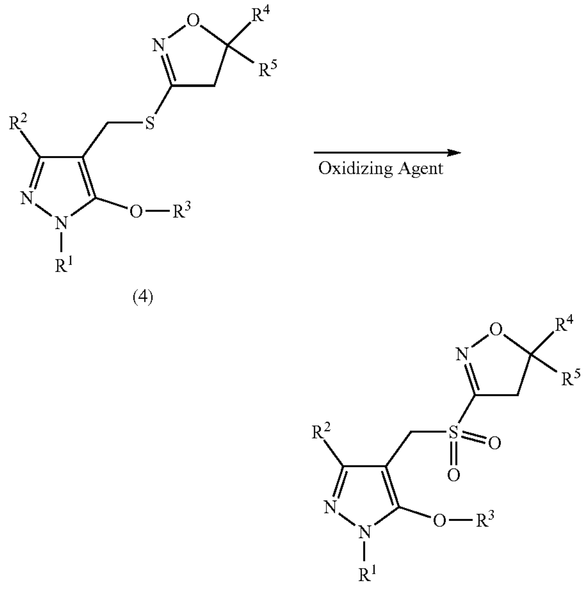

(4)

(5)

wherein $R^1$, $R^2$, $R^3$, $R^4$ and $R^5$ are each independently a (C1-C6)alkyl optionally substituted with one or more substituents.

[53] The process according to [52], wherein the reaction in the step iii is performed in the presence of a metal catalyst.

[54] The process according to [52], wherein the oxidizing agent in the step iii is hydrogen peroxide.

The specifications described in [6] to [51] can be applied to [52] to [54] unless inconsistent.

Advantageous Effects of Invention

The present invention provides a novel compound of formula (2) having pest control activity.

The present invention further provides a novel process for producing a compound of formula (4) useful as a production intermediate of a herbicide and a compound of formula (5) (particularly, pyroxasulfone) that is a herbicide, and provides a compound of formula (2) that is an intermediate thereof. The process of the present invention can safely produce the compound of formula (4) and the compound of formula (5), and is useful. The process of the present invention is suitable for industrial production because the production can be performed without using special manufacturing equipment, special reaction conditions and special expensive reagents.

As compared with a sulfur-containing organic compound having distinctive strong bad smell, disulfide compounds produced in Examples 4 to 6 of the present invention have substantially no bad smell. Besides, these disulfide compounds are solids having sufficiently high melting points. A high melting point means that the compound is preferable for storage, and that a choice of recrystallization is provided as an isolation process and/or a purification process.

The disulfide compound of the present invention has been found to simultaneously have such a plurality of advantages.

DESCRIPTION OF EMBODIMENTS

The symbols and terms described in the present description will be explained.

Herein, the following abbreviations and prefixes may be used, and their meanings are as follows:

Me: methyl
n-: normal
s- and sec-: secondary
i- and iso-: iso
t- and tert-: tertiary
c- and cyc-: cyclo
o-: ortho
m-: meta
p-: para The term "nitro" means the substituent "—$NO_2$".

The term "cyano" means the substituent "—CN".

The term "hydroxy" means the substituent "—OH".

The term "amino" means the substituent "—$NH_2$".

Herein, it is to be interpreted that generic terms such as "alkyl" include both the straight chain and the branched chain such as butyl and tert-butyl. Meanwhile, for example, the specific term "butyl" refers to straight "normal butyl", and does not refer to branched "tert-butyl". Branched chain isomers such as "tert-butyl" are referred to specifically when intended.

Examples of the halogen atom include fluorine atom, chlorine atom, bromine atom and iodine atom.

The (C1-C6)alkyl means a straight or branched alkyl having 1 to 6 carbon atoms. Examples of the (C1-C6)alkyl include, but are not limited to, methyl, ethyl, propyl, isopropyl, butyl, sec-butyl, isobutyl, tert-butyl, pentyl and hexyl.

The (C1-C4)alkyl means a straight or branched alkyl having 1 to 4 carbon atoms. Examples of the (C1-C4)alkyl include, appropriate examples of the examples of the (C1-C6)alkyl above-mentioned.

Herein, there are no particular limitations on the "substituent(s)" for the phrase "optionally substituted with one or more substituents" as long as they are chemically acceptable and exhibit the effects of the present invention.

Herein, examples of the "substituent(s)" for the phrase "optionally substituted with one or more substituent(s)" include, but are not limited to, one or more substituents (preferably 1 to 3 substituents) selected independently from Substituent Group (a).

Substituent Group (a) is a group consisting of a halogen atom; a nitro group, a cyano group, a hydroxy group, an amino group, (C1-C6)alkyl, and phenyl.

In addition, one or more substituents (preferably 1 to 3 substituents) selected independently from Substituent Group (a) may each independently be substituted with one or more substituents (preferably 1 to 3 substituents) selected independently from Substituent Group (b). In this context, Substituent Group (b) is the same as Substituent Group (a).

Examples of the (C1-C4)alkyl optionally substituted with 1 to 9 fluorine atoms include, but are not limited to, fluoromethyl (i.e., $—CH_2F$), difluoromethyl (i.e., $—CHF_2$), trifluoromethyl (i.e., $—CF_3$), 2-fluoroethyl, 2,2,2-trifluoroethyl, pentafluoroethyl, 3-fluoropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 4-fluorobutyl, 2,2,3,3,4,4,4-heptafluorobutyl, nonafluorobutyl, 1,1,2,3,3,3-hexafluoro-2 trifluoromethylpropyl and 2,2,2-trifluoro-1,1-di(trifluoromethyl)ethyl.

The (C1-C4)perfluoroalkyl means a straight or branched alkyl having 1 to 4 carbon atoms, wherein all hydrogen atoms are substituted with fluorine atoms. Examples of the (C1-C4)perfluoroalkyl are trifluoromethyl (i.e., $—CF_3$), pentafluoroethyl (i.e., $—CF_2CF_3$), heptafluoropropyl (i.e., $—CF_2CF_2CF_3$), 1,2,2,2-tetrafluoro-1-trifluoromethylethyl (i.e., $—CF(CF_3)_2$), nonafluorobutyl, (i.e., $—CF_2CF_2CF_2CF_3$), 1,2,2,3,3,3-hexafluoro-1-trifluoromethylpropyl (i.e., $—CF(CF_3) CF_2CF_3$), 1,1,2,3,3,3-hexafluoro-2-trifluoromethylpropyl (i.e., $—CF_2CF(CF_3)_2$) and 2,2,2-trifluoro-1,1-di(trifluoromethyl) ethyl (i.e., $—C(CF_3)_3$).

Herein, the phrase "as described herein" and similar phrases used when referring to substituents (for example, $R^1$, $R^2$, $R^3$, $R^4$, $R^5$, $X^1$ and $X^2$) incorporate by reference all definitions of the substituents and, if any, all of their examples, preferred examples, more preferred examples, further preferred examples and particularly preferred examples in this specification.

Unless otherwise stated, all technical and scientific terms used herein have the same meaning as commonly understood by a person skilled in the art to which the present disclosure belongs.

As used herein, the non-limiting term "comprise(s)/comprising" can each optionally be replaced by the limiting phrase "consist(s) of/consisting of".

Herein, the term "using" can optionally be replaced by the term "in the presence of" unless inconsistent.

Herein, the term "in the presence of" can optionally be replaced by the term "using" unless inconsistent.

Unless otherwise indicated, it is understood that numbers used herein to express characteristics such as quantities, sizes, concentrations, and reaction conditions are modified by the term "about". In some embodiments, disclosed numerical values are interpreted applying the reported number of significant digits and conventional rounding techniques. In some embodiments, disclosed numerical values are interpreted as containing certain errors necessarily resulting from the standard deviation found in their respective testing measurements.

The term "pest control agent" means an insecticide, an acaricide, a nematicide and the like of the fields of agriculture and horticulture for animals such as domestic animals and pets, for home use, or for epidemic prevention.

A compound of the present invention will now be described. A compound of the following formula (2) has pest control activity, and is useful as an active ingredient of a pest control agent.

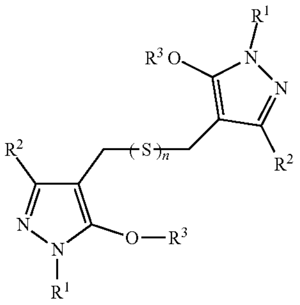

(2)

From the viewpoint of usefulness of the compound, $R^1$ is a (C1-C6)alkyl optionally substituted with one or more substituents, preferably a (C1-C4)alkyl, and more preferably methyl in formula (2).

$R^2$ is a (C1-C6)alkyl optionally substituted with one or more substituents, preferably a (C1-C4)perfluoroalkyl, and more preferably trifluoromethyl.

$R^3$ is a (C1-C6)alkyl optionally substituted with one or more substituents, preferably a (C1-C4)alkyl optionally substituted with 1 to 9 fluorine atoms, and more preferably difluoromethyl.

n is, but not limited to, an integer of 1 or more, preferably an integer of 2 to 5, more preferably 2 or 3, and further preferably 2.

The compound of formula (2) may be a mixture of a disulfide compound wherein n is 2, and a polysulfide compound wherein n is 3 or more, and such a mixture is within the scope of the present invention. For example, the compound of formula (2) may be any mixture of a group of compounds wherein n is any integer of 1 or more, may be any mixture of a group of compounds wherein n is any integer of 2 to 5, or may be any mixture of a group of compounds wherein n is 2 and 3. Such a mixture is within the scope of the present invention.

Preferable specific examples of the compound of formula (2) include, but are not limited to, the following:

(2-a)

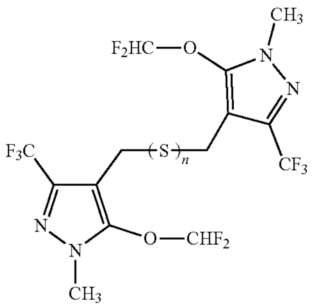

A process for producing the compound of formula (2) will now be described. Besides, a process for producing a compound of formula (4) using the compound of formula (2) will be described.

The process for producing the compound of formula (2) of the present invention is as follows:

A process for producing the compound of formula (2) from a compound of formula (1), in other words, a process including producing the compound of formula (2) using the compound of formula (1):

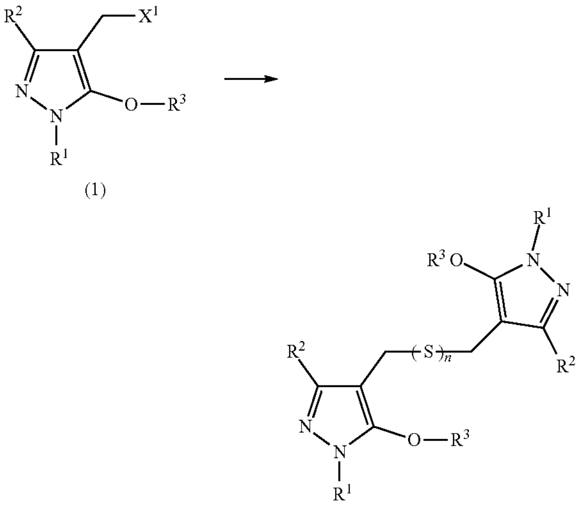

(1)

(2)

wherein $R^1$, $R^2$, $R^3$, $X^1$ and n are as described herein.

(Step i)

A step i will now be described.

The step i is one of processes for producing the compound of formula (2).

The step i is a step of producing the compound of formula (2) by reacting the compound of formula (1) with a sulfur compound.

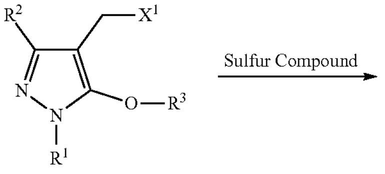

(1)

-continued

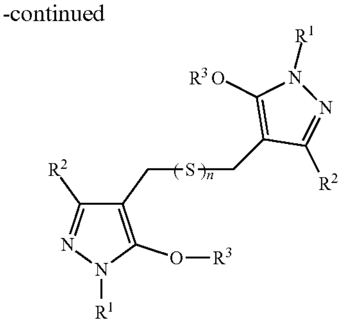

(2)

wherein $R^1$, $R^2$, $R^3$ and n are as described herein, and $X^1$ is a halogen atom.

(Raw Material in Step i: Compound of Formula (1))

As a raw material in the step i, the compound of formula (1) is used.

The compound of formula (1) is a known compound, or can be produced from a known compound in accordance with a known process (such as WO 2004/013106 A1 or WO 2021/002484 A9).

From the viewpoints of usefulness, economic efficiency and the like of the product, $R^1$, $R^2$, and $R^3$ in formula (1) are as defined in formula (2). Examples, preferred examples, more preferred examples, and particularly preferred examples and the like of $R^1$, $R^2$ and $R^3$ in formula (1) are, if any, the same as those in formula (2) described above.

$X^1$ is a halogen atom, preferably a chlorine atom or a bromine atom, and more preferably a chlorine atom.

Preferable specific examples of the compound of formula (1) include, but are not limited to, the following:

(1-a)

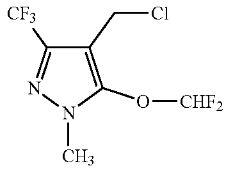

(1-b)

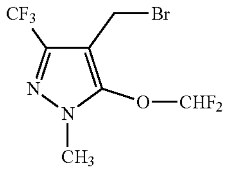

From the viewpoint of economic efficiency and the like, the compound (1-a) is more preferable.

(Product in Step i: Compound of Formula (2))

The product in the step i is a compound of formula (2) corresponding to the compound of formula (1) used as a raw material.

The compound of formula (2) is described above, and the product produced in the step i is the compound of formula (2). The product produced in the step i is a disulfide compound wherein n is 2 in formula (2). In some cases, however, a polysulfide compound wherein n is 3 or more may be produced. Specifically, the product produced in the step i may be obtained as a mixture of compounds wherein n is 2 or more in formula (2). A disulfide compound wherein n is 2, and a polysulfide compound wherein n is 3 or more will probably provide, through the subsequent step ii, the compound of formula (4) (such as ISFP) of the same product. Accordingly, the mixture of a disulfide compound wherein n is 2 and a polysulfide compound wherein n is 3 or more can probably be used as a raw material in the subsequent step ii directly without isolation/purification. On the other hand, in general, when purification is necessary, a salt has a problem that purification with water washing is difficult to employ because of its water solubility. The compound of formula (2) can be, however, purified with water washing. Besides, a salt has concerns of deliquescency during storage in general, but the compound of formula (2) is advantageously free from such concerns. In addition, in the present invention, a high-purity product can be obtained through a post-treatment operation well known to a person skilled in the art such as extraction or crystal washing, namely, through a simple operation. Furthermore, the compound of formula (2), particularly the compound of formula (2-a) can have a feature of excellent storage stability.

A preferable specific example of the disulfide compound of formula (2) includes, but is not limited to, the following:

(2-a)

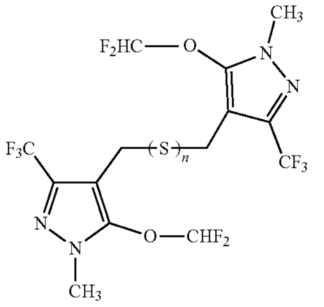

(Sulfur Compound in Step i)

Examples of the sulfur compound in the step i include, but are not limited to, an inorganic sulfur compound, sulfur, an inorganic sulfur compound and sulfur, thiourea, a substituted thiourea, a thiocarboxylate, a thioamide, a thiosulfate, and a xanthate salt.

The step i may be a step i-a, or a step i-b.

(Step i-a)

The step i-a is a step of obtaining the compound of formula (2) by reacting the compound of formula (1) with an inorganic sulfur compound.

The step i-a is preferably a step of obtaining the compound of formula (2) by reacting the compound of formula (1) with an inorganic sulfur compound and sulfur.

(Inorganic Sulfur Compound in Step i-a)

In one aspect, examples of the inorganic sulfur compound in the step i-a include, but are not limited to, sodium sulfide, potassium sulfide, sodium hydrosulfide, potassium hydrosulfide, sodium disulfide, potassium disulfide, and a mixture thereof, preferably sodium sulfide and sodium disulfide, and more preferably sodium sulfide. In another aspect, examples of the inorganic sulfur compound in the step i-a preferably include sodium sulfide, potassium sulfide, and a mixture thereof, and more preferably sodium sulfide.

The inorganic sulfur compound in the step i-a can be used singly or in a combination of two or more, and is preferably used in combination with sulfur. The amount of the inorganic sulfur compound in the step i-a is, for example, 0.5 to 5 mol, and preferably 0.5 to 2 mol based on 1 mol of the compound of formula (1) (raw material). The amount of the sulfur is, for example, 0.25 to 5 mol, preferably 0.5 to 2 mol, and more preferably 0.5 to 1 mol based on 1 mol of the compound of formula (1) (raw material). The form of the inorganic sulfur compound in the step i-a may be any form as long as the reaction proceeds. Examples of the form of the inorganic sulfur compound in the step i-a include a solid of its own, and an aqueous solution with any concentration (of, for example, 10 to 50%). The inorganic sulfur compound in the step i-a may be a hydrate. The form of the sulfur in the step i-a may be any form as long as the reaction proceeds. Examples of the form of the sulfur in the step i-a include a solid, a viscous liquid, and a liquid.

Step i-b)

The step i-b is a step of producing the compound of formula (2) by reacting the compound of formula (1) with a sulfur compound, hydrolyzing the resultant, and then reacting the resultant with an oxidizing agent:

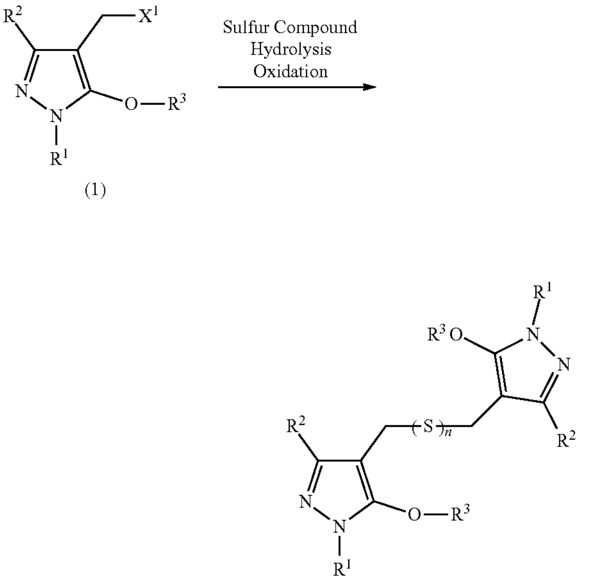

(1)

(2)

wherein $R^1$, $R^2$, $R^3$, $X^1$ and n are as described herein.

The step i-b is, for example, a step of obtaining the compound of formula (2) by reacting the compound of formula (1) with thiourea, hydrolyzing the resultant, and then reacting the resultant with an oxidizing agent:

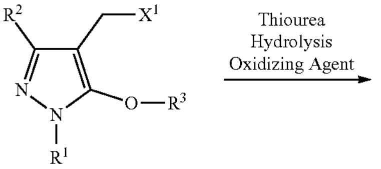

(1)

-continued

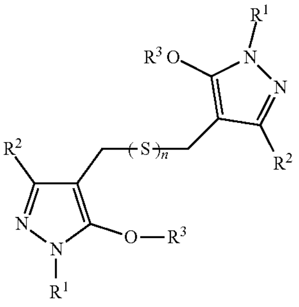

(2)

wherein $R^1$, $R^2$, $R^3$, $X^1$ and n are as described herein.

Examples of the sulfur compound in the step i-b include, but are not limited to, the following:

thiourea;

substituted thioureas, preferably N,N'-dialkylthioureas and N-monoalkylthioureas (e.g., N,N'-dimethylthiourea, N,N'-diethylthiourea, N,N'-diphenylthiourea, N-methylthiourea, N-ethylthiourea, and N-phenylthiourea);

thiocarboxylates, preferably thioacetates (e.g., potassium thioacetate, and sodium thioacetate);

thioamides (e.g., N,N-dimethylthioformamide, thiobenzamide, and dithiooxamide);

thiosulfates (e.g., sodium thiosulfate, and potassium thiosulfate); and xanthate salts (e.g., potassium ethylxanthate, sodium ethylxanthate, potassium methylxanthate, and sodium methylxanthate).

Examples of an intermediate optionally obtained in the reaction with the sulfur compound include, but are not limited to, the following:

In the following formulas, Ra is a (C1-C6)alkyl, or phenyl optionally substituted with one or more (preferably one to two, and more preferably one) selected from the group consisting of a (C1-C6)alkyl and a halogen atom (preferably a chlorine atom); and $R^b$ is hydrogen, a (C1-C6)alkyl, or phenyl optionally substituted with one or more (preferably one to two, and more preferably one) selected from the group consisting of a (C1-C6)alkyl and a halogen atom (preferably a chlorine atom).

(Int-1)

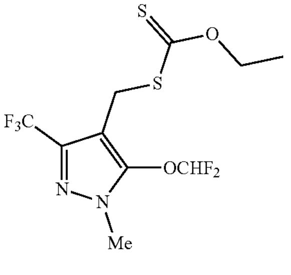

-continued (Int-2-1)

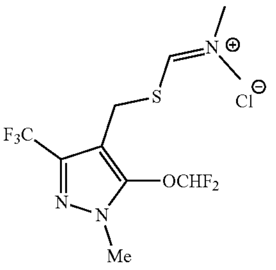

(Int-2-2)

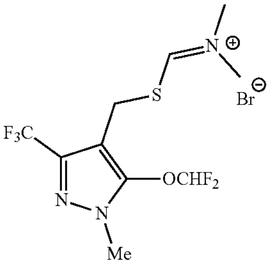

(Int-3-1)

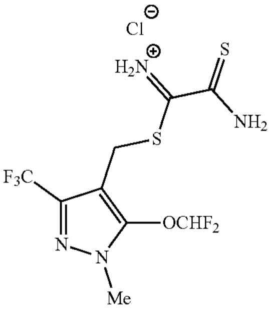

(Int-3-2)

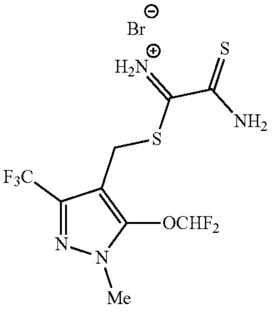

(Int-4)

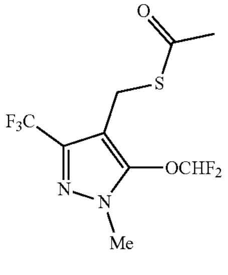

-continued (Int-5-1)

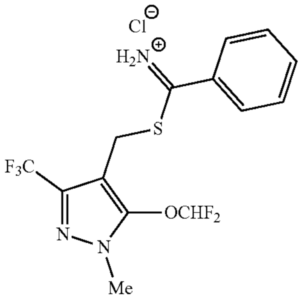

(Int-5-2)

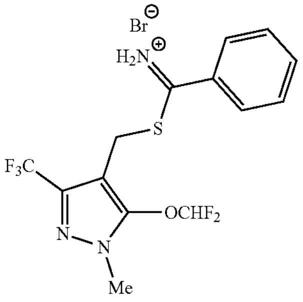

(Int-6)

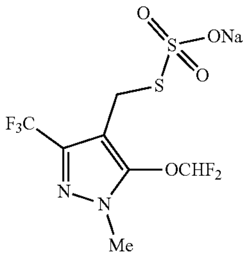

(Int-7-1)

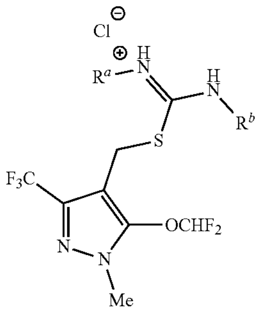

(Int-7-2)

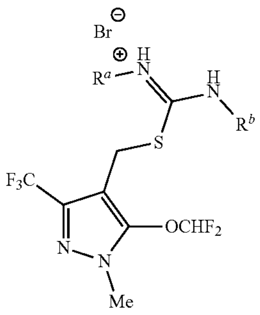

-continued (Int-8-1)

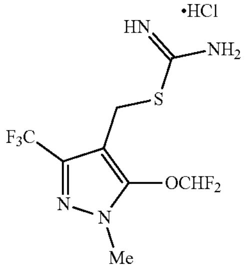

(TMTP—HCl)

(Int-8-2)

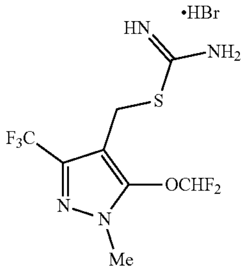

(TMTP—HBr)

The amount of the sulfur compound (for example, thiourea) in the step i-b is, for example, 1 to 2 mol, and preferably 1.0 to 1.5 mol based on 1 mol of the compound of formula (1) (raw material).

For example, the hydrolysis is preferably performed in the presence of a base. Examples of the base include, but are not limited to, sodium hydroxide, potassium hydroxide, calcium hydroxide, sodium carbonate, potassium carbonate, sodium bicarbonate, potassium bicarbonate, calcium bicarbonate, sodium phosphate, and potassium phosphate, and preferably sodium hydroxide, potassium hydroxide, sodium carbonate, and potassium carbonate. Sodium hydroxide or potassium hydroxide is more preferable, and sodium hydroxide is further preferable. The amount of the base is, for example, 2 to 5 mol, and preferably 2 to 3 mol based on 1 mol of the compound of formula (1) (raw material).

It is preferable that, for example, after the hydrolysis with a base, the resultant reaction mixture is neutralized with an acid, and the resultant is then reacted with an oxidizing agent (namely, oxidized). Examples of the acid include, but are not limited to, hydrochloric acid, sulfuric acid, acetic acid, methanesulfonic acid, trifluoromethanesulfonic acid, p-toluenesulfonic acid, and phosphoric acid, and preferably hydrochloric acid and sulfuric acid. Hydrochloric acid is more preferable. The amount of the acid can be appropriately adjusted by a person skilled in the art.

Examples of the oxidizing agent in the step i-b include, but are not limited to, hydrogen peroxide, hypochlorite, peroxide, permanganate, manganese dioxide, and oxygen including the air and the like, and preferably include hydrogen peroxide. The amount of the oxidizing agent is, for example, 0.2 to 1.5 mol, and preferably 0.3 to 1.0 mol based on 1 mol of the compound of formula (1) (raw material). In view of safety, danger, economic efficiency, and the like, a preferred example of the form of the hydrogen peroxide in the step i-b includes a 10 to 70 wt % aqueous hydrogen peroxide solution, and more preferably a 25 to 65 wt % aqueous hydrogen peroxide solution.

The reaction solvent, the reaction temperature, the reaction time, and the like in the reaction in the step i, namely, the reaction in the step i-a (the reaction with an inorganic sulfur compound and the reaction with an inorganic sulfur compound and sulfur), and the reaction in the step i-b (the reaction of thiourea or the like with the sulfur compound, the hydrolysis, and the oxidation) will now be described. These are as follows:

(Reaction Solvent in Step i)

The reaction in the step i may be performed in the absence or presence of a solvent. Whether or not to use a solvent in the reaction in the step i can be appropriately determined by a person skilled in the art. When the solvent is used in the reaction in the step i, the solvent of the reaction in the step i can be appropriately selected by a person skilled in the art as long as the reaction proceeds. Examples of the solvent of the reaction in the step i include, but are not limited to, the following: water, aromatic hydrocarbon derivatives (e.g., benzene, toluene, xylene, chlorobenzene, dichlorobenzene, trichlorobenzene and nitrobenzene), halogenated aliphatic hydrocarbons (e.g., dichloromethane, chloroform and 1,2-dichloroethane (EDC)), alcohols (e.g., methanol, ethanol, 2-propanol, butanol, and tert-butanol (tert-butanol is also referred to as tert-butyl alcohol)), nitriles (e.g., acetonitrile and propionitrile), ethers (e.g., tetrahydrofuran (THF), 1,4-dioxane, diisopropyl ether, dibutyl ether, di-tert-butyl ether, cyclopentyl methyl ether (CPME), methyl tert-butyl ether, 1,2-dimethoxyethane (DME) and diglyme), amides (e.g., N,N-dimethylformamide (DMF), N,N-dimethylacetamide (DMAC) and N-methylpyrrolidone (NMP)), ureas (e.g., N,N'-dimethylimidazolidinone (DMI) and tetramethylurea), sulfoxides (e.g., dimethyl sulfoxide (DMSO)), and any combination thereof in any ratio. It may be understood that the reaction solvent includes solvents in a raw material solution and a reactant solution. In other words, it may be understood that solvents in a raw material solution and a reactant solution are "solvents of the reaction". For example, it may be understood that water in an aqueous sodium hydroxide solution used in the reaction is a reaction solvent. As another example, it may be understood that water in an aqueous hydrogen peroxide solution used in the reaction is a reaction solvent.

Examples of the solvent of the reaction in the step i-a preferably include a combination of a halogenated aliphatic hydrocarbon and water, and a combination of an amide and water. The combination of an amide and water is more preferable. Here, the halogenated aliphatic hydrocarbon is preferably dichloromethane, chloroform, or a mixture thereof. Here, the amide is preferably N,N-dimethylformamide (DMF), N,N-dimethylacetamide (DMAC), or a mixture thereof, and more preferably N,N-dimethylformamide (DMF). A combination of N,N-dimethylformamide and water is particularly preferable.

Examples of the solvent of the reaction in the step i-b preferably include a combination of an alcohol and water, and a combination of a nitrile and water. Here, the alcohol is preferably methanol, ethanol, 2-propanol, or a mixture thereof, and more preferably methanol, ethanol, or a mixture thereof. Here, the nitrile is preferably acetonitrile.

The amounts of the solvents used in the reaction in the step i, namely, the reaction in the step i-a (the reaction with an inorganic sulfur compound and the reaction with an inorganic sulfur compound and sulfur), and the reaction in the step i-b (the reaction of thiourea or the like with the sulfur compound, the hydrolysis, and the oxidation) will now be described. These reaction solvents are as described above. The amount of the solvent used in the reaction in the step i is not particularly limited as long as the reaction system can be sufficiently stirred. From the viewpoints of yield, suppression of by-products, economic efficiency, and the like, however, the amount of the solvent used in the reaction in the step i is, for example, 0 (zero) L to 10 L, preferably 0.1 L to 10 L, and more preferably 0.2 L to 5 L based on 1 mol of the compound of formula (1) (raw material). When a combination of two or more solvents is used, the ratio of the two or more solvents may be any ratio as long as the reaction proceeds.

(Reaction Temperature in Step i)

The reaction temperature in the step i is not particularly limited. However, from the viewpoint of yield, suppression of by-products, economic efficiency, etc., the reaction temperature in the step i is, for example, −10° C. (minus 10° C.) to 100° C., preferably 0° C. (zero ° C.) to 80° C., more preferably 0° C. to 70° C., further preferably 10° C. to 70° C.

(Reaction Time in Step i)

The reaction time in the step i is not particularly limited. However, from the viewpoint of yield, suppression of by-products, economic efficiency, etc., the reaction time in the step i is, for example, 0.5 hours to 48 hours, preferably 0.5 hours to 24 hours. The reaction time can be adjusted appropriately by a person skilled in the art.

The compound of the formula (2), especially the compound (2-a), which is the product in the step i, can be used as a raw material in the step ii.

(Step ii)

The step ii will be described.

The step ii is a step of producing the compound of formula (4) by reacting the compound of formula (2) with a compound of formula (3):

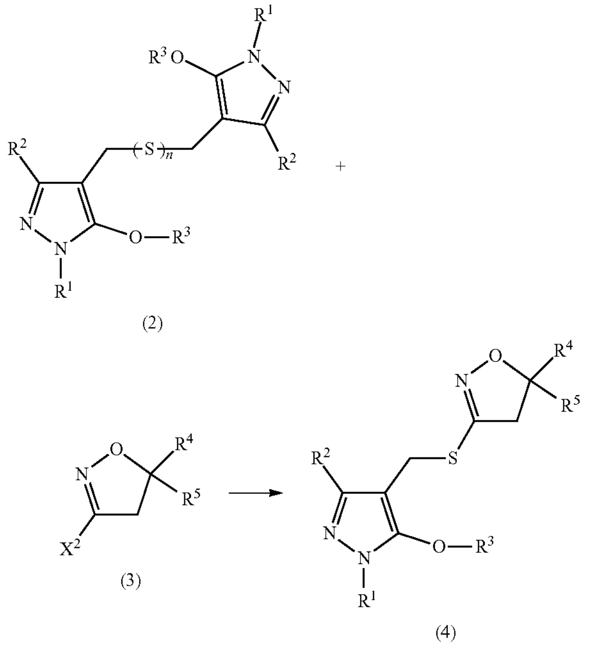

(2) (3) (4)

wherein $R^1$, $R^2$, $R^3$, $R^4$, $R^5$, $X^2$ and n are as described herein.

Herein, the expression that "the compound of formula (4) is produced by reacting the compound of formula (2) with the compound of formula (3)" and a similar expression can be replaced by expression that "the compound of formula (4) is produced from the compound of formula (2) and the compound of formula (3)". The present invention encompasses "a process for producing the compound of formula (4) from the compound of formula (2) and the compound of formula (3)".

In one aspect, the step ii is a step of producing the compound of formula (4) by reacting the compound of formula (2) with the compound of formula (3) in the presence of a reducing agent. In another aspect, the step ii is a step of producing the compound of formula (4) by reacting the compound of formula (2) with the compound of formula (3) using a reducing agent.

In one aspect, the reaction in the step ii is more preferably performed in the presence of a reducing agent and a base. In another aspect, the reaction in the step ii is more preferably performed using a reducing agent in the presence of a base.

In still another aspect, the reaction in the step ii is performed in the presence of a reducing agent or a base.

In one aspect, the reaction in the step ii is further preferably performed in the presence of a reducing agent, an inorganic sulfur compound, and a base. In another aspect, the reaction in the step ii is more preferably performed using a reducing agent and using an inorganic sulfur compound in the presence of a base.

(Raw Material in Step ii: Compound of Formula (2))

The compound of formula (2) is as described above, a raw material used in the step ii is the compound of formula (2), and the product produced in the step i can be used. A disulfide compound wherein n is 2, and a polysulfide compound wherein n is 3 or more will probably provide, in the step ii, the compound of formula (4) of the same product. Accordingly, the mixture of a disulfide compound wherein n is 2 and a polysulfide compound wherein n is 3 or more can probably be used as a raw material in the step ii directly without isolation.

(Raw Material in Step ii: Compound of Formula (3))

As a raw material in the step ii, the compound of formula (3) is used.

From the viewpoint of usefulness, economic efficiency, and the like of the product, in formula (3), $R^4$ is a (C1-C6) alkyl optionally substituted with one or more substituents, preferably a (C1-C4)alkyl, and more preferably methyl.

$R^5$ is a (C1-C6)alkyl optionally substituted with one or more substituents, preferably a (C1-C4)alkyl, and more preferably methyl.

$X^2$ is a halogen atom, preferably a chlorine atom or a bromine atom, and more preferably a chlorine atom.

The compound of formula (3) is a known compound, or can be produced from a known compound according to a known process. For example, the preparation of the compound of formula (3) can be performed by a process described in Reference Examples 1 and 2 of WO 2006/068092 A1, or by a process similar thereto.

From the viewpoint of usefulness and the like of the product, preferable specific examples of the compound of formula (3) include, but are not limited to, the following: 3-chloro-5,5-dimethyl-4,5-dihydroisoxazole (3-a, ClO), and 3-bromo-5,5-dimethyl-4,5-dihydroisoxazole (3-b, BIO). From the viewpoint of economic efficiency and the like, 3-chloro-5,5-dimethyl-4,5-dihydroisoxazole (3-a, ClO) is more preferable.

(Raw material in Step ii: Amount of Compound of Formula (3) Used)

The amount of the formula (3) used in the step ii may be any amount as long as the reaction proceeds. The amount of the formula (3) used in the step ii may be appropriately adjusted by a person skilled in the art. However, from the viewpoint of yield, suppression of by-products, economic efficiency, etc., the amount of the compound of the formula (3) used in the step ii is, for example, 2 to 4 mol, preferably 2 to 3 mol, based on 1 mol of the compound of the formula (2) (raw material).

(Product in Step ii; Compound of Formula (4))

The product in the step ii is a compound of the formula (4) corresponding to the compound of the formula (2) and the compound of the formula (3) used as raw materials.

In the formula (4), $R^1$, $R^2$ and $R^3$ are as defined in the formula (1). In the formula (4), $R^4$ and $R^5$ are as defined in the formula (3). In the formula (4), examples, preferred examples, more preferred examples, and particularly preferred examples of $R^1$, $R^2$, $R^3$, $R^4$ and $R^5$ are, if any, the same as those in the formula (1) and the formula (3) described above, respectively.

Particularly preferred specific examples of the compound of the formula (4) are as follows:

(4-a)

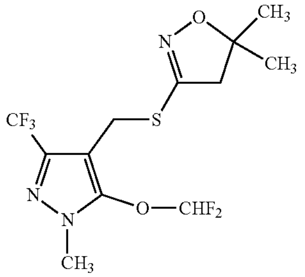

(Reducing Agent in Step ii)

The reducing agent used in the step ii may be any reducing agent as long as the reaction proceeds. Examples of the reducing agent used in the step ii include, but are not limited to, borohydride compounds (e.g., lithium borohydride, sodium borohydride, sodium cyanoborohydride, sodium triacetoxyborohydride, lithium tri-(sec-butyl)borohydride, lithium triethylborohydride, potassium borohydride, and tetramethylammonium borohydride), alkali metal sulfides (e.g., sodium sulfide, and potassium sulfide), alkali metal sulfites (e.g., sodium sulfite, and potassium sulfite), alkali metal bisulfites (e.g., sodium bisulfite, and potassium bisulfite), alkali metal hydroxymethanesulfinates (e.g., sodium hydroxymethanesulfinate), and hyposulphites (e.g., sodium hyposulphite). Examples of the reducing agent in the step ii preferably include an alkali metal hydroxymethanesulfinate and a borohydride compound, and more preferably sodium hydroxymethanesulfinate and sodium borohydride.

Sodium hydroxymethanesulfinate is also designated as sodium formaldehyde sulfoxylate. The sodium hydroxymethanesulfinate may be an anhydride or a hydrate as long as the reaction proceeds, and from the viewpoint of reactivity, availability, and handleability, is preferably sodium hydroxymethanesulfinate dihydrate (trade name: Rongalit) that is a dihydrate.

The reducing agent in the step ii may be used singly or in a combination of two or more kinds thereof in any ratio. The form of the reducing agent in the step ii may be any form as long as the reaction proceeds. The form of the reducing agent can be appropriately selected by a person skilled in the art. Examples of the form of the reducing agent in the step ii include a solid of its own, and an aqueous solution with any concentration (of, for example, 5 to 50%). The reducing agent in the step ii may be a hydrate.

(Amount of Reducing Agent Used in Step ii)

The amount of the reducing agent used in the step ii may be any amount as long as the reaction proceeds. From the viewpoint of yield, suppression of by-products, economic efficiency, and the like, in one aspect, the amount is, for example, usually 0.1 to 10 mol, preferably 1 to 8 mol, more preferably 2 to 6 mol, further preferably 2 to 4 mol, and particularly preferably 2 to 3 mol based on 1 mol of the compound of formula (2).

(Inorganic Sulfur Compound in Step ii)

In one aspect, the reaction in the step ii is preferably performed in the presence of an inorganic sulfur compound. In another aspect, the reaction in the step ii is preferably performed using an inorganic sulfur compound. Any inorganic sulfur compound may be used as the inorganic sulfur compound as long as the reaction proceeds.

Examples of the inorganic sulfur compound include, but are not limited to, sodium sulfide, potassium sulfide, sodium hydrosulfide, potassium hydrosulfide, sodium disulfide, potassium disulfide, and a mixture thereof, preferably sodium hydrosulfide, potassium hydrosulfide, and a mixture thereof, and more preferably sodium hydrosulfide.

The inorganic sulfur compound may be used singly or in a combination of two or more kinds thereof in any ratio. The form of the inorganic sulfur compound in the step ii may be any form as long as the reaction proceeds. Examples of the form of the inorganic sulfur compound in the step ii include a solid, and an aqueous solution with any concentration. The inorganic sulfur compound in the step ii may be a hydrate. The purity (i.e., the concentration) of the inorganic sulfur compound in the step ii is, for example, 10% to 100%, and preferably 50% to 100%. The amount of the inorganic sulfur compound is, for example, 0.5 to 5 mol, and preferably 1 to 2 mol based on 1 mol of the compound of formula (2) (raw material).

(Base in Step ii)

The reaction in the step ii is preferably performed in the presence of a base. The base may be any base as long as the reaction proceeds. Examples of the base in the step ii include, but are not limited to, the following:

alkali metal hydroxides (e.g., lithium hydroxide, sodium hydroxide and potassium hydroxide), alkaline earth metal hydroxides (e.g., magnesium hydroxide, calcium hydroxide and barium hydroxide), alkali metal carbonates (e.g., lithium carbonate, sodium carbonate, potassium carbonate and cesium carbonate), alkaline earth metal carbonates (e.g., magnesium carbonate and calcium carbonate), alkali metal hydrogen carbonates (e.g., lithium hydrogen carbonate, sodium hydrogen carbonate and potassium hydrogen carbonate), alkaline earth metal hydrogen carbonates (e.g., calcium hydrogen carbonate), phosphate salts (e.g., sodium phosphate, potassium phosphate and calcium phosphate), hydrogen phosphate salts (e.g., sodium hydrogen phosphate, potassium hydrogen phosphate and calcium hydrogen phosphate), amines (e.g., triethylamine, tributylamine, diisopropylethylamine, 1,8-diazabicyclo [5.4.0]-7-undec-7-ene (DBU), 1,4-diazabicyclo[2.2.2] octane (DABCO), pyridine and 4-(dimethylamino)-pyridine (DMAP)), ammonia, and a mixture thereof. The examples of the base in the step ii preferably include alkali metal carbonates, alkali metal hydroxides, and a mixture thereof, more preferably sodium carbonate, potassium carbonate, sodium hydroxide, potassium hydroxide, and a mixture thereof, and further preferably potassium carbonate and sodium hydroxide.

The base in the step ii may be used singly or in a combination of two or more kinds thereof in any ratio. The base in the step ii may be in any form as long as the reaction proceeds. Examples of the form of the base in the step ii include a base-only solid and an aqueous solution with any concentration. Specific examples of the form of the base include, but are not limited to, flake, pellet, bead, powder and 10 to 50% aqueous solution, and preferably 20 to 50% aqueous solution (e.g., 25% aqueous sodium hydroxide solution and 48% aqueous sodium hydroxide solution, preferably 48% aqueous sodium hydroxide solution). The form of the base in the step ii can be appropriately selected by a person skilled in the art.

The amount of the base used in the step ii may be any amount as long as the reaction proceeds. The amount of the base used in the step ii is, however, from the viewpoint of yield, suppression of by-products, economic efficiency, and the like, 0 (zero) to 15 mol, preferably 1 to 15 mol, more preferably 3 to 10 mol, and further preferably 3 to 5 mol based on 1 mol of the compound of formula (2) (raw material).

(Adding Method in Step ii)

The order of adding the raw material, the reducing agent, the base, the inorganic sulfur compound, the solvent, and the like, is not particularly limited. The order of adding these may be any order as long as the reaction proceeds. After adding any two or more of these to be reacted, the rest may be added to be reacted. Preferable processes have been found in the present invention. These processes are described herein.

(Reaction Solvent in Step ii)

From the viewpoint of allowing the reaction to smoothly proceed, the reaction in the step ii is preferably performed in the presence of a solvent. The solvent in the reaction in the step ii may be any solvent as long as the reaction proceeds.

Examples of the solvent used in the reaction in the step ii include, but are not limited to, the following:

aromatic hydrocarbon derivatives (e.g., benzene, toluene, xylene, chlorobenzene, dichlorobenzene, trichlorobenzene and nitrobenzene), halogenated aliphatic hydrocarbons (e.g., dichloromethane and 1,2-dichloroethane (EDC)), alcohols (e.g., methanol, ethanol, isopropanol, butanol and tert-butanol (tert-butanol is also referred to as tert-butyl alcohol)), nitriles (e.g., acetonitrile and propionitrile), carboxylic acid esters (e.g., methyl acetate, ethyl acetate, propyl acetate, isopropyl acetate, butyl acetate and isomers thereof, and pentyl acetate and isomers thereof), ethers (e.g., tetrahydrofuran (THF), 1,4-dioxane, diisopropyl ether, dibutyl ether, di-tert-butyl ether, cyclopentyl methyl ether (CPME), methyl tert-butyl ether, 1,2-dimethoxyethane (DME) and diglyme), ketones (e.g., acetone, methyl ethyl ketone (MEK), methyl isopropyl ketone (MIPK) and methyl isobutyl ketone (MIBK)), amides (e.g., N,N-dimethylformamide (DMF), N,N-dimethylacetamide (DMAC), and N-methylpyrrolidone (NMP)), ureas (e.g., N,N'-dimethylimidazolidinone (DMI) and tetramethylurea), sulfoxides (e.g., dimethyl sulfoxide (DMSO)), sulfones (e.g., sulfolane), water, and any combination of these in any ratio.

Preferable examples include a combination of an alcohol, an amide and water, a combination of an alcohol and water, and a combination of an amide and water. Here, the alcohol is preferably methanol, ethanol, 2-propanol, or a mixture thereof, and more preferably methanol, ethanol, or a mixture thereof. Here, the amide is preferably N,N-dimethylformamide (DMF), N,N-dimethylacetamide (DMAC), or a mixture thereof, and more preferably N,N-dimethylformamide (DMF). In one aspect, a combination of N,N-dimethylformamide and water is particularly preferable.

When a borohydride compound is used as the reducing agent, an alcohol is preferably used. In this case, the alcohol may be used in combination with another solvent.

The reaction solvent may be understood to include solvents in a raw material solution and a reactant solution. In other words, it may be understood that solvents in a raw material solution and a reactant solution are "solvents of the reaction".

In any case, the solvent may be in a single layer or may be separated into two layers as long as the reaction proceeds.

The amount of the solvent used in the reaction in the step ii is not particularly limited as long as the reaction system can be sufficiently stirred. From the viewpoint of yield, suppression of by-products, economic efficiency, and the like, however, the amount of the solvent used in the reaction in the step ii is, for example, 0 (zero) L to 10 L, preferably 0.2 L to 8 L, more preferably 0.5 L to 8 L, and further preferably 1 L to 8 L based on 1 mol of the compound of formula (2) (raw material). When two or more solvents are used in combination, the ratio of the two or more solvents is any ratio as long as the reaction proceeds.

(Reaction Temperature in Step ii)

The reaction temperature in the step ii is not particularly limited. From the viewpoint of yield, suppression of by-products, economic efficiency, and the like, however, the reaction temperature in the step ii is, for example, −10 (minus 10°) C to 100° C., preferably 0 (zero)° C. to 90° C., and more preferably 10° C. to 70° C. In one aspect, it is further preferably 10° C. to 60° C. In another aspect, it is further preferably 40° C. to 70° C., and still further preferably 40° C. to 60° C.

(Reaction Time in Step ii)

The reaction time in the step ii is not particularly limited. From the viewpoint of yield, suppression of by-products, economic efficiency, and the like, however, the reaction time in the step ii is, for example, 1 hour to 48 hours, preferably 2 hours to 48 hours, and more preferably 4 hours to 36 hours. The reaction time can be adjusted appropriately by a person skilled in the art.

(Step iii)

The step iii will now be described.

The step iii is one of processes for producing the compound of formula (5), which can be produced from the compound of formula (4) according to a known process (WO 2021/0002484 A1, WO 2022/191292 A1, or WO 2022/138781 A1) although not limited thereto. The step iii is, for example, as follows:

(Step iii) A step of producing the compound of formula (5) by reacting the compound of formula (4) with an oxidizing agent:

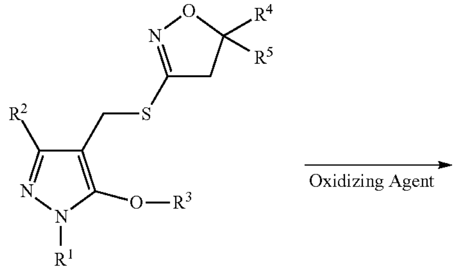

(4)

-continued

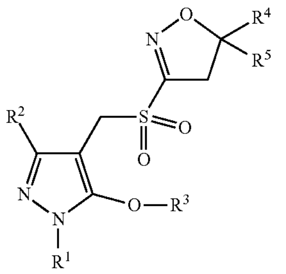

(5)

wherein $R^1$, $R^2$, $R^3$, $R^4$ and $R^5$ are as described herein.

(Raw Material in Step iii: Compound of Formula (4))

As the raw material in the step iii, the compound of formula (4) is used. The compound of formula (4) is as described above.

In formula (4), $R^1$, $R^2$, and $R^3$ are as defined in formula (1). In formula (4), $R^4$ and $R^5$ are as defined in formula (3). In formula (4), examples, preferred examples, more preferred examples, and particularly preferred examples of $R^1$, $R^2$, $R^3$, $R^4$, and $R^5$ in formula (4) are, if any, the same as those in formulas (1) and (3) described above.

A particularly preferable specific example of the compound of formula (4) is a compound of the following formula (4-a):

(4-a)

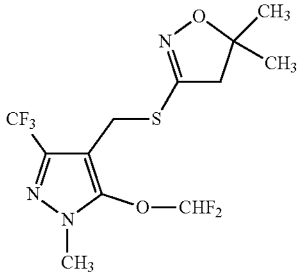

(Product in Step iii; Compound of Formula (5))

The product in the step iii is a compound of the formula (5) corresponding to the compound of the formula (4) used as a raw material.

In the formula (5), $R^1$, $R^2$ and $R^3$ are as defined in the formula (1). In the formula (5), $R^4$ and $R^5$ are as defined in the formula (3). In the formula (5), examples, preferred examples, more preferred examples, and particularly preferred examples of $R^1$, $R^2$, $R^3$, $R^4$ and $R^5$ are the same as those in the formula (1) and the formula (3) described above, respectively.

Particularly preferred specific examples of the compound of the formula (5) are as follows:

(5-a)

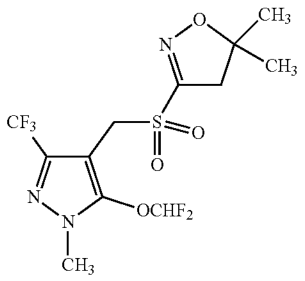

Pyroxasulfone (Oxidizing Agent in Step iii: Hydrogen Peroxide)

In the reaction in the step iii, hypochlorites (e.g., sodium hypochlorite, and potassium hypochlorite), peroxides (e.g., hydrogen peroxide, sodium bisulfate, sodium persulfate (sodium peroxodisulfate), potassium persulfate, ammonium persulfate, potassium bisulfate (potassium peroxymonosulfate, Oxone (registered trademark))), permanganate, manganese dioxide, chromic acid and the like can be used as the oxidizing agent. Hydrogen peroxide is preferably used.

In view of safety, danger, economic efficiency, and the like, an example of the form of hydrogen peroxide in the step iii preferably includes a 10 to 70 wt % aqueous hydrogen peroxide solution, and more preferably a 25 to 65 wt % aqueous hydrogen peroxide solution.

From the viewpoints of yield, suppression of by-products, economic efficiency, safety, danger, and the like, the amount of the hydrogen peroxide used in the step iii is, for example, 2 mol or more, and preferably 2 to 8 mol based on 1 mol of the compound of formula (4) (raw material).

(Catalyst in Step iii: Metal Catalyst)

The reaction in the step iii can be performed in the presence of or in the absence of a metal catalyst. When a metal catalyst is used, the metal catalyst may be any metal catalyst as long as the reaction proceeds. Examples of the metal catalyst in the step iii include, but are not limited to, the following: tungsten catalysts (e.g., tungstic acid, tungstic acid salts (e.g., sodium tungstates (including sodium tungstate dihydrate and the like), potassium tungstate, and ammonium tungstate), metal tungsten, tungsten oxide, tungsten carbide, and tungsten chloride), molybdenum catalysts (e.g., molybdic acid, molybdic acid salts (e.g., sodium molybdate (including sodium molybdate dihydrate), potassium molybdate, ammonium molybdate (including ammonium molybdate tetrahydrate)), metal molybdenum, molybdenum oxide, and molybdate chloride), and niobium catalysts (e.g., niobium carbide, niobium(V) chloride and niobium(V) pentaethoxide). Examples of the metal catalyst preferably include tungsten catalysts and molybdenum catalysts, and more preferably sodium tungstate and ammonium molybdate.

When the metal catalyst is used, the amount of the metal catalyst used in the step iii is any amount as long as the reaction proceeds. From the viewpoint of yield, suppression of by-products, economic efficiency, and the like, the use amount thereof is, for example, 0.001 to 0.1 mol, and preferably 0.01 to 0.05 mol based on 1 mol of the compound of formula (4) (raw material).

The reaction in the step iii may be performed in the presence of an acid catalyst such as sulfuric acid or phenyl phosphate. Besides, the reaction in the step iii may be performed in the presence of a phase transfer catalyst such as tetrabutylammonium hydrogen sulfate. The use amount thereof is, but not limited to, for example, 0 (zero) to 0.3 mol, 0.001 to 0.1 mol, 0.01 to 0.05 mol, or any combination of these upper limits and lower limits based on 1 mol of the compound of formula (4) (raw material).

The reaction in the step iii may be performed in the presence of or the absence of the metal catalyst under acidic conditions. In this case, sulfuric acid or a carboxylate (e.g., acetic acid, dichloroacetic acid, trichloroacetic acid, or trifluoroacetic acid) is preferably used. The carboxylate may be used as a solvent. The sulfuric acid or carboxylate may be a salt thereof. The use amount thereof is, but not limited to, for example, 0 (zero) to 100 mol, 0.001 to 10 mol, 0.01 to 5 mol, or any combination of these upper limits and lower limits based on 1 mol of the compound of formula (4) (raw material).

The reaction in the step iii may be performed in the absence of the metal catalyst under basic conditions. In this case, an alkali metal carbonate (e.g., sodium carbonate or potassium carbonate) or an alkali metal bicarbonate (e.g., sodium bicarbonate or potassium bicarbonate) is preferably used. The use amount thereof is, but not limited to, for example, 0 (zero) to 10 mol, 0.01 to 5 mol, 0.1 to 1 mol, or any combination of these upper limits and lower limits based on 1 mol of the compound of formula (4) (raw material).

The reaction in the step iii may be a combination of a reaction under acidic conditions and a reaction under basic conditions.

(Reaction Solvent in Step iii)

From the viewpoint of allowing the reaction to smoothly proceed, the reaction in the step iii is preferably performed in the presence of an organic solvent. Examples of the organic solvent in the reaction in the step iii include, but are not limited to, the following:

alcohols (e.g., methanol, ethanol, 2-propanol, butanol and tert-butanol (tert-butanol is also referred to as tert-butyl alcohol)), nitriles (e.g., acetonitrile and propionitrile), carboxylic acid esters (e.g., methyl acetate, ethyl acetate, propyl acetate, isopropyl acetate, butyl acetate and isomers thereof, and pentyl acetate and isomers thereof), amides (e.g., N,N-dimethylformamide (DMF), N,N-dimethylacetamide (DMAC), and N-methylpyrrolidone (NMP)), carboxylic acids (e.g., acetic acid, dichloroacetic acid, trichloroacetic acid, and trifluoroacetic acid), and any combination of these in any ratio. In addition, the reaction in the step iii is more preferably performed in the presence of an organic solvent and a water solvent, although not limited thereto. The organic solvent includes organic solvents in a raw material solution and a reactant solution. The water solvent includes water in a raw material solution and a reactant solution (e.g., water in an aqueous hydrogen peroxide solution).

In any case, the solvent may be in a single layer or may be separated into two layers as long as the reaction proceeds.

The total amount of the solvents used in the reaction in the step iii is not particularly limited as long as the reaction system can be sufficiently stirred. From the viewpoint of yield, suppression of by-products, economic efficiency, and the like, however, the amount of the solvents used in the reaction in the step iii is, for example, 0.1 L to 10 L, and preferably 0.3 L to 5 L based on 1 mol of the compound of formula (4) (raw material). When two or more solvents are used in combination, the ratio of the two or more solvents is any ratio as long as the reaction proceeds.

(Reaction Temperature in Step iii)

The reaction temperature in the step iii is not particularly limited. From the viewpoint of yield, suppression of by-products, economic efficiency, and the like, however, the reaction temperature in the step ii is, for example, 0 (zero)° C. to 100° C., and preferably 50° C. to 90° C.

(Reaction Time in Step iii)

The reaction time in the step iii is not particularly limited. From the viewpoint of yield, suppression of by-products, economic efficiency, and the like, however, the reaction time in the step ii is, for example, 1 hour to 48 hours, and preferably 4 hours to 24 hours. The reaction time can be adjusted appropriately by a person skilled in the art.

The reactions in all the steps of the present invention may be each independently performed by a batch method, or a flow method.

The pest control agent of the present invention can contain an additive component (carrier) usually used in an agrochemical formulation as desired, and can be produced as an agrochemical composition containing an active ingredient and an agrochemically acceptable carrier.

Examples of the additive component include a carrier such as a solid carrier or a liquid carrier, a surfactant, a binder or a tackifier, a thickener, a colorant, a spreader, a sticker, an antifreezer, an anticaking agent, a disintegrating agent, and a stabilizing agent, and a preservative, a plant piece or the like may be used as the additive component as desired. Besides, one of these additive components may be singly used, or two or more of these may be used in combination.

The additive component will now be described.

Examples of the solid carrier include mineral carriers such as pyrophyllite clay, kaolin clay, silica stone clay, talc, diatomite, zeolite, bentonite, acid clay, activated clay, Attapalgas clay, vermiculite, perlite, pumice, white carbon (synthetic silicic acid, synthetic silicate, and the like), and titanium dioxide; plant carriers such as wood flour, cornstalk, walnut shells, fruit kernels, rice hulls, sawdust, bran, soybean flour, powdered cellulose, starch, dextrin, and saccharides; inorganic salt carriers such as calcium carbonate, ammonium sulfate, sodium sulfate, and potassium chloride; and polymer carriers such as polyethylene, polypropylene, polyvinyl chloride, polyvinyl acetate, an ethylene-vinyl acetate copolymer, and a urea-aldehyde resin.

Examples of the liquid carrier include monohydric alcohols such as methanol, ethanol, propanol, 2-propanol, butanol, and cyclohexanol; polyhydric alcohols such as ethylene glycol, diethylene glycol, propylene glycol, hexylene glycol, polyethylene glycol, polypropylene glycol, and glycerin; polyhydric alcohol derivatives such as propylene-based glycol ether; ketones such as acetone, methyl ethyl ketone, methyl isobutyl ketone, diisobutyl ketone, cyclohexanone, and isophorone; ethers such as diethyl ether, 1,4-dioxane, cellosolve, dipropyl ether, and tetrahydrofuran; aliphatic hydrocarbons such as normal paraffin, naphthene, isoparaffin, kerosene, and mineral oil; aromatic hydrocarbons such as toluene, $C_9$-$C_{10}$ alkylbenzene, xylene, solvent naphtha, alkyl naphthalene, and high-boiling point aromatic hydrocarbon; halogenated hydrocarbons such as 1,2-dichloroethane, chloroform, and carbon tetrachloride; esters such as ethyl acetate, diisopropyl phthalate, dibutyl phthalate, dioctyl phthalate, and dimethyl adipate; lactones such as γ-butyrolactone; amides such as N,N-dimethylformamide, N,N-diethylformamide, N,N-dimethylacetamide, and N-methyl-2-pyrrolidone; nitriles such as acetonitrile; sulfur compounds such as dimethylsulfoxide; vegetable oils such as soybean oil, rapeseed oil, cottonseed oil, coconut oil, and castor oil, and fatty acid lower alkyl esters derived from these vegetable oils; and water.

Examples of the surfactant include nonionic surfactants such as sorbitan fatty acid esters, polyoxyethylene sorbitan fatty acid esters, sucrose fatty acid esters, polyoxyethylene fatty acid esters, polyoxyethylene resin acid esters, polyoxyethylene fatty acid diesters, polyoxyethylene alkyl ethers, polyoxyethylene alkyl phenyl ethers, polyoxyethylene dialkyl phenyl ethers, polyoxyethylene alkyl phenyl ether formalin condensates, polyoxyethylene polyoxypropylene block polymers, alkyl polyoxyethylene polypropylene block polymer ethers, polyoxyethylene alkyl amines, polyoxyethylene fatty acid amides, polyoxyethylene fatty acid bisphenyl ethers, polyalkylene benzyl phenyl ethers, polyoxyalkylene styryl phenyl ethers, acetylenediols, polyoxyalkylene-added acetylenediols, polyoxyethylene ether-type silicones, ester-type silicones, fluorine-based surfactants, polyoxyethylene castor oil, and polyoxyethylene hydrogenated castor oil; anionic surfactants such as alkyl sulfates, polyoxyethylene alkyl ether sulfates, polyoxyethylene alkyl phenyl ether sulfates, polyoxyethylene styryl phenyl ether sulfates, alkyl benzenesulfonates, lignosulfonates, alkyl sulfosuccinates, naphthalene sulfonates, alkyl naphthalene sulfonates, salts of formalin condensates of naphthalene sulfonates, salts of formalin condensates of alkyl naphthalene sulfonates, fatty acid salts, polycarboxylates, N-methyl-fatty acid sarcosinates, resin acid salts, polyoxyethylene alkyl ether phosphates, and polyoxyethylene alkyl phenyl ether phosphates; cationic surfactants such as alkylamine salts such as laurylamine hydrochloride, stearylamine hydrochloride, oleylamine hydrochloride, stearylamine acetate, stearylaminopropylamine acetate, alkyltrimethylammonium chloride, and alkyldimethylbenzalkonium chloride; and amphoteric surfactants of betaine-type such as dialkyldiaminoethylbetaine, and alkyldimethylbenzylbetaine, and of amino acid-type such as dialkylaminoethylglycine, and alkyldimethylbenzylglycine.

Examples of the binder or the tackifier include carboxymethyl cellulose and salts thereof, dextrin, water-soluble starch, xanthan gum, guar gum, sucrose, polyvinyl pyrrolidone, gum arabic, polyvinyl alcohol, polyvinyl acetate, sodium polyacrylate, polyethylene glycol, polyethylene oxide, and natural phospholipids (e.g., cephalic acid, and lecithin).

Examples of the thickener include water-soluble polymers such as xanthan gum, guar gum, carboxymethyl cellulose, polyvinyl pyrrolidone, carboxyvinyl polymers, acrylic polymers, starch derivatives, and polysaccharides; and inorganic fine powders such as high-purity bentonite and white carbon, and organic fine powders such as organic bentonite.

Examples of the colorant include inorganic pigments such as iron oxide, titanium oxide, and Prussian blue; and organic dyes such as alizarin dyes, azo dyes, and metal phthalocyanine dyes.

Examples of the spreader include silicone-based surfactants, cellulose powders, dextrin, modified starch, polyaminocarboxylic acid chelate compounds, crosslinked polyvinyl pyrrolidone, maleic acid/styrene copolymers, methacrylic acid copolymers, half esters of polyhydric alcohol polymers and dicarboxylic anhydride, water-soluble salts of polystyrenesulfonic acid, polyoxyethylene alkanediols, polyoxyethylene alkynediols, and alkynediols.

Examples of the sticker include various surfactants such as sodium dialkyl sulfosuccinates, polyoxyethylene alkyl ethers, polyoxyethylene alkyl phenyl ethers, and polyoxyethylene fatty acid esters; and paraffin, terpene, polyamide resins, polyacrylates, polyoxyethylene, waxes, polyvinyl alkyl ethers, alkylphenol formalin condensates, and synthetic resin emulsions.

Examples of the antifreezer include polyhydric alcohols such as ethylene glycol, diethylene glycol, propylene glycol, and glycerin.

Examples of the anticaking agent include polysaccharides such as starch, alginic acid, mannose, and galactose; and polyvinyl pyrrolidone, white carbon, ester gum, and petroleum resins.

Examples of the disintegrating agent include sodium tripolyphosphate, sodium hexametaphosphate, metal stearates, cellulose powders, dextrin, copolymers of methacrylates, polyvinyl pyrrolidone, polyaminocarboxylic acid chelate compounds, sulfonated styrene-isobutylene-maleic anhydride copolymers, and starch-polyacrylonitrile graft copolymers.

Examples of the stabilizing agent include desiccants such as zeolite, quicklime, and magnesium oxide; phenol-based, amine-based, sulfur-based, and phosphate-based antioxidants; and salicylic acid-based, and benzophenone-based UV absorbers.

Examples of the preservative include potassium sorbate, and 1,2-benzothiazol-3(2H)-one.

Examples of the plant piece include sawdust, coconut shells, corn cobs, and tobacco stems.

On the other hand, when the pest control agent of the present invention contains the above-described additive component, the content ratio thereof is selected, in terms of mass, from a range of usually 5 to 95% and preferably 20 to 90% for the carrier such as a solid carrier or a liquid carrier, from a range of usually 0.1% to 30% and preferably 0.5 to 10% for the surfactant, and from a range of usually 0.1 to 30% and preferably 0.5 to 10% for the other additives.

The pest control agent of the present invention is formulated, for use, into any formulation such as a powder, a dust and granule, a granule, a wettable powder, a water-soluble powder, a water dispersible granule, a tablet, a jumbo formulation, an emulsifiable concentrate, an oil solution, a liquid, a flowable formulation, a concentrated emulsion, a microemulsion, a suspoemulsion, an ultra low volume dusting powder, a microcapsule, a smoking agent, an aerosol, a bait formulation, or a paste.

In actual use, these formulations can be directly used, or can be used after dilution to a desired concentration with a diluent such as water. Various formulations containing the compound of the present invention or dilutions thereof can be usually applied by a general application method, namely, by dispersing (e.g., spraying, misting, atomizing, powder scattering, granule scattering, application on water surface, or application in a box), soil application (e.g., mixing, or irrigating), surface application (e.g., coating, dust coating, or covering), seed treatment (e.g., smearing, or dust coating treatment), dipping, poison baiting, or fumigation application. Alternatively, the active ingredient can be mixed with feed to be given to domestic animals, so as to use the excrement thereof for controlling generation and growth of pests, particularly pest insects.

A pest control method of the present invention can be performed by using an active ingredient amount of a heterocyclic compound represented by the compound (2-a) of the present invention or an agriculturally acceptable salt thereof by any of the above-described application methods.

The blending ratio (% by mass) of the active ingredient in the pest control agent of the present invention is appropriately selected as desired. For example, when the agent is in the form of a dust, a dust and granule, a fine granule or the like, the ratio may be appropriately selected from a range of 0.01 to 20%, and preferably 0.05 to 10%, when in the form of a granule or the like, the ratio may be appropriately selected from a range of 0.1 to 30%, and preferably 0.5 to 20%, when in the form of a wettable powder, a water-soluble powder or the like, the ratio may be appropriately selected from a range of 1 to 70%, and preferably 5 to 50%, when in the form of a water-soluble powder, a liquid or the like, the ratio may be appropriately selected from a range of 1 to 95%, and preferably 10 to 80%, when in the form of an emulsifiable concentrate or the like, the ratio may be appropriately selected from a range of 5 to 90%, and preferably 10 to 80%, when in the form of an oil solution or the like, the ratio may be appropriately selected from a range of 1 to 50%, and preferably 5 to 30%, when in the form of a flowable formulation or the like, the ratio may be appropriately selected from a range of 5 to 60%, and preferably 10 to 50%, when in the form of a concentrated emulsion, a microemulsion, a suspoemulsion or the like, the ratio may be appropriately selected from a range of 5 to 70%, and preferably 10 to 60%, when in the form of a tablet, a bait formulation, a paste or the like, the ratio may be appropriately selected from a range of 1 to 80%, and preferably 5 to 50%, when in the form of a smoking agent or the like, the ratio may be appropriately selected from a range of 0.1 to 50%, and preferably 1 to 30%, and when in the form of an aerosol or the like, the ratio may be appropriately selected from a range of 0.05 to 20%, and preferably 0.1 to 10%.

These formulations are diluted to an appropriate concentration to be diffused, or directly applied.

The application of the pest control agent of the present invention is, when it is diluted with a diluent for use, performed at an active ingredient concentration of generally 0.1 to 5000 ppm. When the formulation is directly used, the application amount per unit area is, but not limited to, 0.1 to 5000 g per ha in terms of the amount of the active ingredient compound.

It goes without saying that the pest control agent of the present invention is sufficiently effective even when the compound of the present invention is singly used as the active ingredient, but as desired, it can be used as a mixture with or used together with another fertilizer or pesticide, such as an insecticide, a nematicide, a miticide, a synergist, a fungicide, an antiviral agent, an attractant, a herbicide, a plant growth regulator or the like, and further excellent effects may be exhibited in this case.

Hereinafter, the present invention will be described in more detail by Examples, but the present invention is not limited in any way by these Examples.

In the present description, the following instruments and conditions were used for the determination of physical properties and yields in Examples, Comparative Examples and Reference Examples. In addition, identification was conducted in the usual manner known to a person skilled in the art.

(HPLC Analysis: High Performance Liquid Chromatography Analysis)

(HPLC Analysis Conditions)

Instrument: LC 2010 Series manufactured by Shimadzu Corporation or any equivalent thereto Column: YMC-Pack, ODS-A, A-312 (150 mm×6.0 mm ID, S-5 μm, 120 A)

Eluent:

TABLE 1

| Time (min) | Acetonitrile (%) | 0.085% Aqueous Phosphoric Acid Solution (%) |
|---|---|---|
| 0 | 45 | 55 |
| 5 | 45 | 55 |
| 15 | 100 | 0 |
| 20 | 100 | 0 |

Flow rate: 1.0 ml/min

Detection: UV 230 nm

Column temperature: 40° C.

Injection volume: 5 μL

The following documents can be referred to for the HPLC analysis method, as desired.

Literature (a): "Shin Jikkenkagaku Koza 9 (A New Course in Experimental Chemistry Course 9) Bunsekikagaku II (Analytical Chemistry II)", pages 86 to 112 (1977), edited by the Chemical Society of Japan, published by Shingo Iizumi, Maruzen Co., Ltd.

Literature (b): "Jikkenkagaku Koza 20-1 (A Course in Experimental Chemistry 20-1), Bunseki Kagaku (Analytical Chemistry)", 5th edition, pages 130 to 151 (2007), edited by the Chemical Society of Japan, published by Seishiro Murata, Maruzen Co., Ltd.

(LC-MS: Liquid Chromatography Mass Spectrometry)

Pump: Agilent 1260 Infinity

Detector: Agilent 6120 Quadropole

Column: CERI L-column ODS (4.6×250 mm), L-C18, 5 μm, 12 nm ($^1$H Nuclear Magnetic Resonance Spectrum ($^1$H-NMR))

Varian Mercury-300

Solvent: $CDCl_3$ and/or DMSO-$d_6$

Internal standard substance: tetramethylsilane (TMS)

(Method for Measuring pH)

The pH was measured with a glass electrode type hydrogen ion concentration meter. As the glass electrode type hydrogen ion concentration meter, for example, model: HM-30P manufactured by DKK-TOA Corporation can be used.

(Method for Measuring Melting Point)

The melting point was measured with a DSC differential scanning calorimeter. The differential scanning calorimetry was performed with DSCvesta (manufactured by Rigaku Corporation) in a temperature range of 10 to 200° C. at a heating rate of 10° C./min. The following documents can be referred to for the differential scanning calorimetry method, as desired.

Literature (a): "Jikkenkagaku Koza 4 (A Course in Experimental Chemistry 4) 4th edition, Netsu and Atsuryoku (Heat and Pressure)", pages 57 to 93 (1992), edited by the Chemical Society of Japan, published by Kumao Ebihara, Maruzen Co., Ltd.

Literature (b): "Jikkenkagaku Koza 6 (A Course in Experimental Chemistry 6) 5th edition, Ondo, Netsu and Atsuryoku (Temperature, Heat and Pressure)", pages 203 to 205 (2005), edited by the Chemical Society of Japan, published by Seishiro Murata, Maruzen Co., Ltd.

(Yield and Purity)

Unless otherwise specified, the yield in the present invention can be calculated from the number of moles of the obtained target compound with respect to the number of moles of the raw material compound (starting compound).

That is, the term "yield" means "molar yield".

Thus, the yield is represented by the following equation:

Yield (%)=(the number of moles of the target compound obtained)/(the number of moles of the starting compound)×100.

However, for example, in the evaluation of the reaction yield of the target product, the yield of impurities, the purity of the product, etc., HPLC area percentage analysis or GC area percentage analysis may be employed.

Herein, room temperature and ordinary temperature are from 10° C. to 30° C.

Herein, the term "overnight" means from 8 hours to 16 hours.

Herein, the procedure of "age/aged/aging" includes stirring a mixture by the usual manner known to a person skilled in the art.

EXAMPLES

Example 1

(Step ii)

Production of 3-[(5-difluoromethoxy-1-methyl-3-trifluoromethylpyrazol-4-yl)methylthio]-4,5-dihydro-5,5-dimethylisoxazole (Compound 4-a, ISFP)

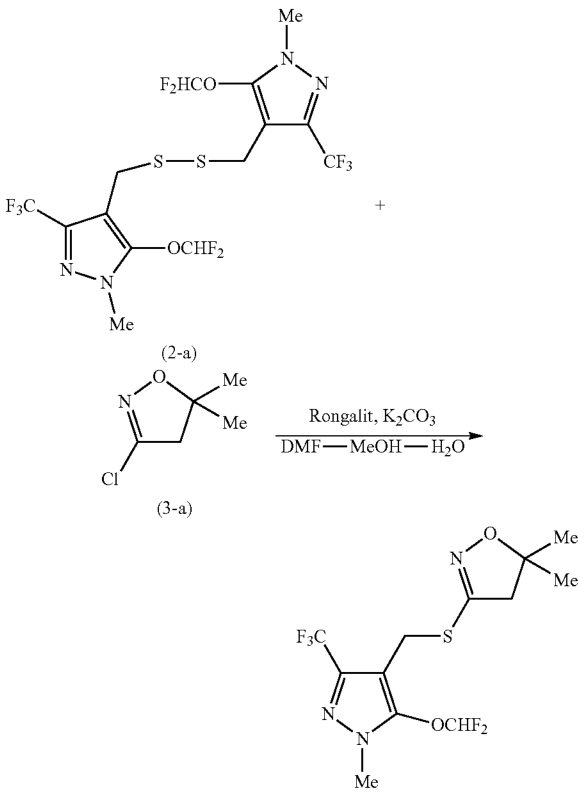

(2-a)

(3-a)

(4-a)

Under a nitrogen stream, 1,2-bis[(5-difluoromethoxy-1-methyl-3-trifluoromethylpyrazol-4-yl)methyl]disulfide (2-a, disulfide compound, 0.12 g, purity: 89%, 0.20 mmol, 100 mol % as 2-a, 200 mol % as a pyrazole moiety) was added to a reaction flask, and dissolved in 0.99 ml of dimethylformamide. To the resultant mixture, 3-chloro-5,5-dimethyl-4,5-dihydroisooxazole (3-a, CIO, 0.34 g, purity: 25%, 0.64 mmol, 310 mol %, containing 0.26 g of methanol), potassium carbonate (0.22 g, 1.6 mmol, 780 mol %), and a Rongalit aqueous solution (0.43 g, purity: 28%, 0.78 mmol, 380 mol %, containing 0.31 g of water) were successively added, followed by stirring at 50° C. for 5 hours and 30 minutes.

As a result of HPLC analysis of the thus obtained reaction mixture, 3-[(5-difluoromethoxy-1-methyl-3-trifluoromethylpyrazol-4-yl)methylthio]-4,5-dihydro-5,5-dimethylisooxazole (compound 4-a, ISFP), which is a target product, was 64% (HPLC area percentage; 230 nm).

Example 2

(Step ii)

Production of 3-[(5-difluoromethoxy-1-methyl-3-trifluoromethylpyrazol-4-yl)methylthio]-4,5-dihydro-5,5-dimethylisoxazole (Compound 4-a, ISFP)

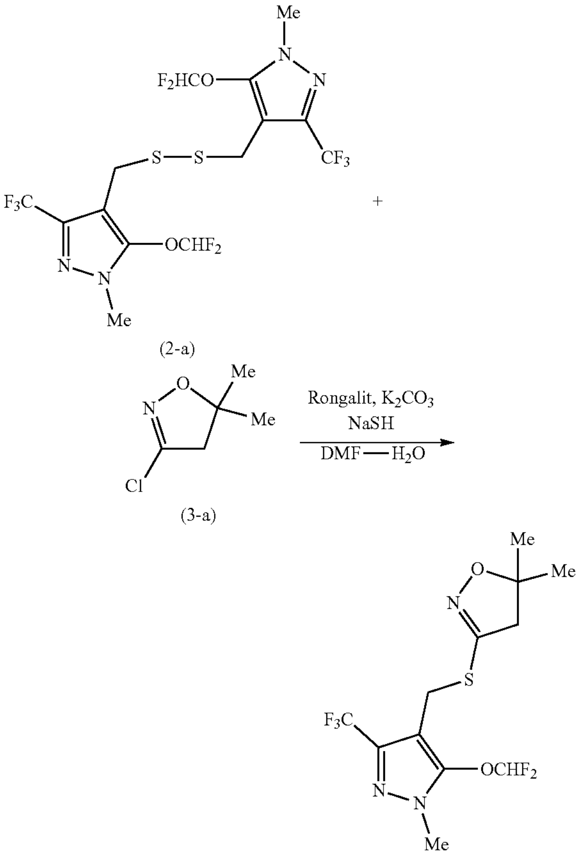

(2-a)

(3-a)

(4-a)

Under a nitrogen stream, 1,2-bis[(5-difluoromethoxy-1-methyl-3-trifluoromethylpyrazol-4-yl)methyl]disulfide (2-a, disulfide compound, 0.10 g, purity: 98%, 0.188 mmol, 100 mol % as 2-a, 200 mol % as a pyrazole moiety) was added to a reaction flask, and dissolved in 0.80 ml of dimethylformamide. To the resultant, potassium carbonate (0.106 g, 0.767 mmol, 409 mol %), sodium hydrosulfide (0.026 g, purity: 65%, 0.30 mmol, 160 mol %) and a Rongalit aqueous solution (0.467 g, purity: 13%, 0.394 mmol, 210 mol %, containing 0.406 g of water) were successively added, followed by stirring at room temperature for 2 hours. To the resultant mixture, 3-chloro-5,5-dimethyl-4,5-dihydroisooxazole (3-a, CIO, 0.267 g, purity: 23%, 0.450 mmol, 240 mol %, containing 0.207 g of dimethylformamide) was added, followed by further stirring at 50° C. for 5 hours.

As a result of HPLC analysis of the thus obtained reaction mixture, 3-[(5-difluoromethoxy-1-methyl-3-trifluoromethylpyrazol-4-yl)methylthio]-4,5-dihydro-5,5-dimethylisooxazole (compound 4-a, ISFP), which is a target product, was 69% (HPLC area percentage; 230 nm), and the yield thereof was 53% (HPLC absolute calibration curve method).

Example 3

(Step ii)

Production of 3-[(5-difluoromethoxy-1-methyl-3-trifluoromethylpyrazol-4-yl)methylthio]-4,5-dihydro-5,5-dimethylisoxazole (Compound 4-a)

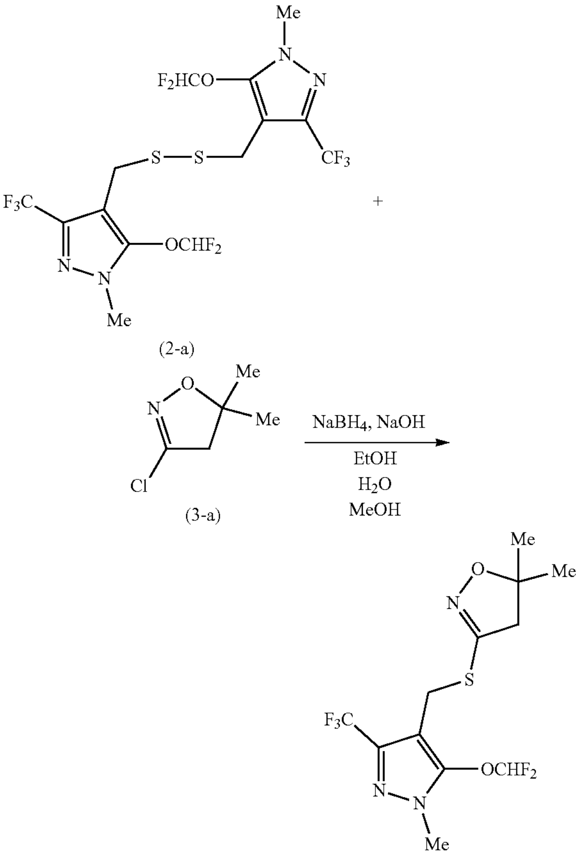

(2-a)

(3-a)

(4-a)

Under a nitrogen stream, 1,2-bis[(5-difluoromethoxy-1-methyl-3-trifluoromethylpyrazol-4-yl)methyl]disulfide (2-a, disulfide compound, 0.10 g, purity: 98%, 0.19 mmol, 100 mol % as 2-a, 200 mol % as a pyrazole moiety) was added to a reaction flask, and dissolved in 0.66 ml of ethanol. To the resultant, an aqueous sodium hydroxide solution (0.120 g, purity: 25%, 0.750 mmol, 400 mol %, containing 0.090 g of water), and sodium borohydride (0.043 g, 1.1 mmol, 600 mol %) were successively added at room temperature, followed by stirring at room temperature for 2 hours. To the resultant mixture, 3-chloro-5,5-dimethyl-4,5-dihydroisooxazole (3-a, CIO, 0.241 g, purity: 25%, 0.451 mmol, 240 mol %, containing 0.181 g of methanol) was added, followed by further stirring at room temperature for 25 hours.

As a result of HPLC analysis of the thus obtained reaction mixture, 3-[(5-difluoromethoxy-1-methyl-3-trifluoromethylpyrazol-4-yl)methylthio]-4,5-dihydro-5,5-dimethylisooxazole (compound 4-a, ISFP), which is a target product, was 73% (HPLC area percentage; 230 nm), and the yield thereof was 57% (HPLC absolute calibration curve method).

Example 4

Production of 1,2-bis[(5-difluoromethoxy-1-methyl-3-trifluoromethylpyrazol-4-yl)methyl]disulfide (2-a-disulfide Compound)

(Preparation of Raw Material 1-a)

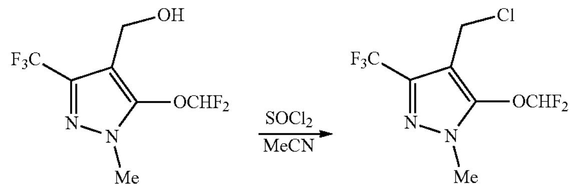

(FMTP) (1-a)

Under a nitrogen stream, 5-difluoromethoxy-4-hydroxymethyl-1-methyl-3-trifluoromethylpyrazole (FMTP, 9.86 g, purity: 97%, 38.9 mmol, 100 mol %) was added to a reaction flask, and dissolved in 16.0 ml of acetonitrile. To the resultant mixture, thionyl chloride (5.35 g, 45 mmol, 116 mol %) was added dropwise at an internal temperature of 15 to 20° C. over 25 minutes, followed by stirring for 1 hour and 30 minutes with the internal temperature maintained at 20° C. to 25° C.

After bubbling nitrogen gas for 1 hour, the resultant was diluted with 40 ml of ethyl acetate. The resultant mixture was washed successively with 30 ml of an aqueous sodium carbonate solution, 30 ml of water, and 30 ml of a saturated sodium chloride solution, and an organic layer was dried over magnesium sulfate. The thus obtained organic layer was distilled off under reduced pressure to obtain 4-chloromethyl-5-difluoromethoxy-1-methyl-3-trifluoromethylpyrazole (1-a, CMTP, 11.14 g, purity: 92%, 38.7 mmol, substantially quantitative) as a yellow oily substance.

(Step i) and (Step i-b)

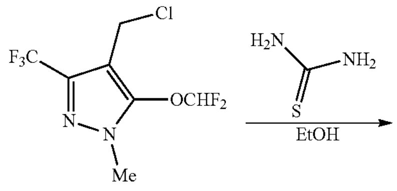

(1-a)

-continued

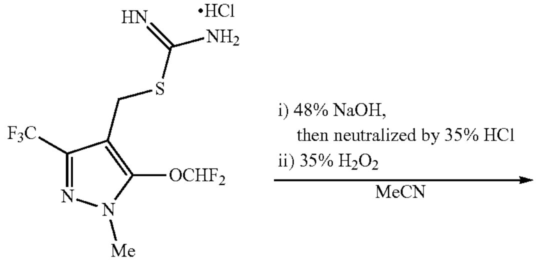

(TMTP-HCl)

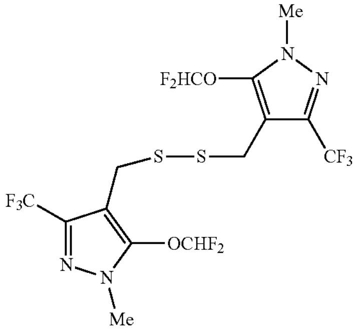

(2-a)
(Disulfide Compound)

To a reaction flask, 4-chloromethyl-5-difluoromethoxy-1-methyl-3-trifluoromethylpyrazole (1-a, CMTP, 7.94 g, purity: 92%, 27.5 mmol, 100 mol %) was added, and dissolved in 17.5 ml of ethanol. To the resultant mixture, thiourea (2.33 g, 30.6 mmol, 111 mol %) was added, followed by stirring at an internal temperature of 50° C. for 3 hours.

To the oily substance obtained by distilling off the solvent under reduced pressure from the mixture, a hexane-ethyl acetate mixed solvent (9:1) was added for performing crystallization. The thus obtained crystals were washed with a hexane-ethyl acetate mixed solvent (4:1), and then was filtered to obtain [(5-difluoromethoxy-1-methyl-3-trifluoromethylpyrazol-4-yl)methyl]thiocarboxamidine hydrochloride (TMTP-HCl, 9.46 g, containing thiourea) as pale yellow crystals, and 8.52 g out of the thus obtained 9.46 g of the crystals was used in the next reaction.

To a reaction flask, the [(5-difluoromethoxy-1-methyl-3-trifluoromethylpyrazol-4-yl)methyl]thiocarboxamidine hydrochloride (8.52 g, containing thiourea) was added, and dissolved in 17.1 ml of acetonitrile. To the resultant mixture, a 48% aqueous sodium hydroxide solution (4.20 g, 50.4 mmol) was added dropwise at an internal temperature of 15 to 20° C. over 15 minutes, followed by stirring at room temperature for 3 hours. A 48% aqueous sodium hydroxide solution (1.40 g, 16.8 mmol) was further added thereto, followed by further stirring at room temperature for 3 hours.

An acetonitrile layer of the resultant mixture was transferred to another reaction flask by decantation using 22.9 ml of another acetonitrile, and then, 3.30 ml of water was added to the resultant acetonitrile solution, and 36% hydrochloric acid was added dropwise thereto to obtain pH 6.02. To the resultant, a 35% aqueous hydrogen peroxide solution (1.01 g, 10.4 mmol) was added dropwise at an internal temperature of 17 to 19° C. over 15 minutes, followed by stirring at an internal temperature of 19 to 21° C. for 1 hour. Water was added to the resultant, the resultant was extracted with toluene, and was washed with an aqueous sodium thiosulfate solution and successively with a saturated sodium chloride solution, and an organic layer was dried over magnesium sulfate.

The thus obtained organic layer was distilled off under reduced pressure, and the residue was purified by silica gel chromatography (hexane:ethyl acetate=4:1 to 1:1) to obtain 4.14 g of colorless crystals. 2.07 g of the crystals were recrystallized with a hexane-ethyl acetate mixed solvent (9:1) to obtain 1.07 g of a disulfide compound as colorless needle crystals. Crystals obtained by concentration in vacuo of the filtrate were washed with a hexane-ethyl acetate mixed solvent (9:1) to obtain 0.23 g of a disulfide compound as colorless crystals. Besides, remaining 2.07 g of the crystals were washed with a hexane-ethyl acetate mixed solvent (9:1) to obtain 1.30 g of the disulfide compound as colorless crystals. Thus, the disulfide compound was obtained in a total amount of 2.60 g (purity: 97%, 4.83 mmol, yield 39% (1-a, 3 steps from CMTP).

($^1$H-NMR Shift of Disulfide Compound)

$^1$H-NMR (300 MHz, $CDCl_3$) δ (ppm, based on TMS) 6.66 (t, J=71.7 Hz, 2H), 3.82 (s, 6H), 3.79 (s, 4H)

(Melting Point of Disulfide Compound)

Melting point: 72.5° C.

(LC-MS Analysis)

Disulfide compound: M+H=523.05

Example 5

(Step i) and (Step i-a)

Production of 1,2-bis[(5-difluoromethoxy-1-methyl-3-trifluoromethylpyrazol-4-yl)methyl]disulfide (2-a, Disulfide Compound)

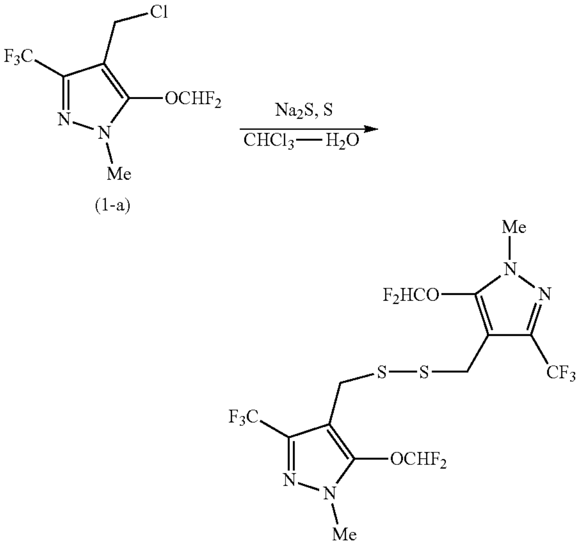

(1-a)

(2-a)

Under a nitrogen stream, sodium sulfide (0.121 g, 1.55 mmol, 157 mol %), sulfur (0.018 g, 0.56 mmol, 57 mol %) and 0.36 ml of water were added to a reaction flask, followed by stirring at an internal temperature of 50° C. for 40 minutes. After cooling the resultant to room temperature, a solution of 4-chloromethyl-5-difluoromethoxy-1-methyl-3-trifluoromethylpyrazole (1-a, CMTP) in chloroform (0.90 g, purity: 29%, 0.99 mmol, containing 0.62 g of chloroform, 100 mol %) was added thereto dropwise over 40 minutes, followed by stirring at room temperature for 15 hours and 30 minutes.

As a result of HPLC analysis of the resultant reaction mixture, the disulfide compound (2-a), which is a target product, was 46.9% (HPLC area percentage; 230 nm).

When the reaction mixture was analyzed by LC-MS, a trisulfide compound was found in addition to the disulfide compound.

(LC-MS Analysis)

Disulfide Compound: M+H=523.05; trisulfide compound: M+H=555.05

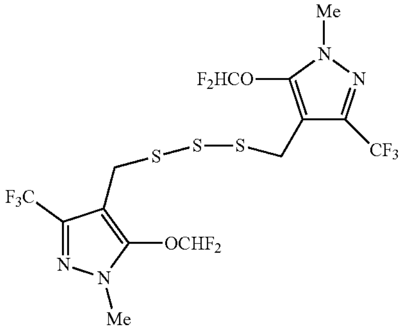

(Trisulfide Compound)

Example 6

(Step i) and (Step i-a)

Production of 1,2-bis[(5-difluoromethoxy-1-methyl-3-trifluoromethylpyrazol-4-yl)methyl]disulfide (2-a, Disulfide Compound)

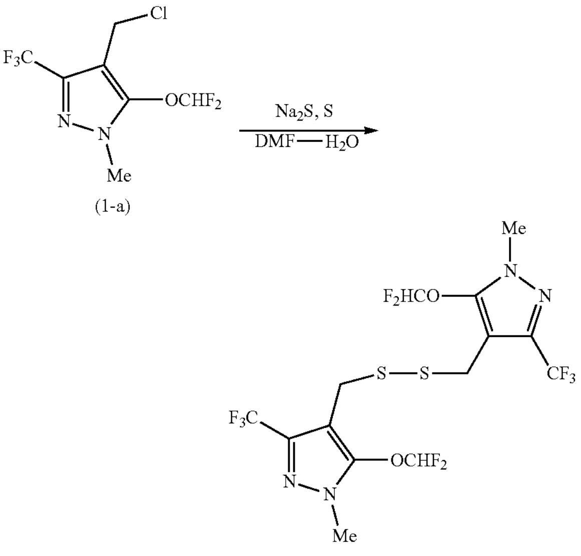

(1-a)

(2-a)

Under a nitrogen stream, sulfur (0.008 g, 0.25 mmol, 50 mol %), 0.81 ml of water, and sodium sulfide (0.029 g, 0.37 mmol, 74 mol %) were successively added to a reaction flask, followed by stirring at 50° C. for 1 hour. After cooling the resultant to room temperature, a solution of 4-chloromethyl-5-difluoromethoxy-1-methyl-3-trifluoromethylpyrazole in dimethylformamide (1-a, CMTP, 0.885 g, purity: 15%, 0.50 mmol, containing 0.752 g of dimethylformamide, 100 mol %) was added thereto dropwise over 1 hour, followed by stirring at room temperature for 1 hour and 30 minutes.

As a result of HPLC analysis of the resultant reaction mixture, the disulfide compound, which is a target product, was 94% (HPLC area percentage; 230 nm), and the yield thereof was 87% (HPLC absolute calibration curve method).

Example 7

Production of 3-[(5-difluoromethoxy-1-methyl-3-trifluoromethylpyrazol-4-yl)methylsulfonyl]-4,5-dihydro-5,5-dimethylisoxazole (Compound 5-a)

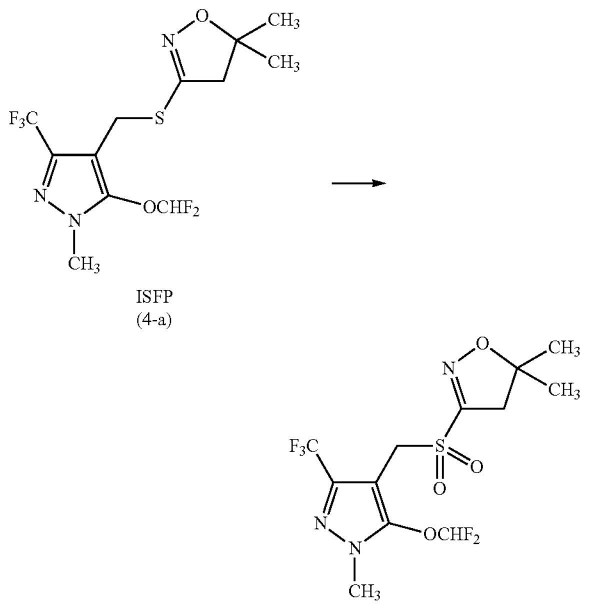

ISFP
(4-a)

Pyroxasulfone
(5-a)

Under a nitrogen stream, a solution of the compound (4-a) in butyl acetate (87.2 g, purity: 41%, 100 mmol, 100 mol %, containing 51.3 g (0.6 L/mol) of butyl acetate), 10 ml (0.1 L/mol) of water and sodium tungstate dihydrate (1.6 g, 5 mmol, 5 mol %) were added to a reaction flask. The mixture was heated to an internal temperature of 70° C. to 80° C. A 35% aqueous hydrogen peroxide solution (27.2 g, 280 mmol, 280 mol %, containing 17.7 g (0.2 L/mol) of water) was added dropwise thereto at an internal temperature of 70° C. to 80° C. over 1 hour, and the mixture was aged for 7 hours while the internal temperature was maintained at 75° C. to 80° C.

A 20% aqueous sodium sulfite solution (31.5 g, 50 mmol, 50 mol %) was added to the reaction mixture, and the resulting mixture was stirred at an internal temperature of 60° C. to 70° C. for 30 minutes. The obtained mixture was separated into an organic layer and an aqueous layer. To the obtained organic layer was added 50 ml (0.5 L/mol) of water, and the mixture was concentrated under reduced pressure. To the obtained crude product was added 133.5 ml (1.7 L/mol) of isopropanol, and crystals were separated by filtration at room temperature. The obtained crystals were washed successively with 12.4 ml (0.2 L/mol) of isopropanol and 10 ml (0.1 L/mol) of water. As a result, crystals of the target product (Compound 5-a) were obtained with a yield of 93%.

$^1$H-NMR value ($CDCl_3$/TMS δ (ppm)) 6.83 (1H, t, J=71.9 Hz), 4.60 (2H, s), 3.88 (3H, s), 3.11 (2H, s), 1.52 (6H, s)

Example 8

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (3.05 g, purity: 100%, 8.5 mmol, 100 mol %), 6.7 g (1.0 L/mol) of methanol, 0.9 ml (0.1 L/mol) of water, and sodium tungstate dihydrate (0.084 g, 0.3 mmol, 3 mol %), and sulfuric acid (0.087 g, 0.85 mmol, 10 mol %) were added to a reaction flask. The mixture was heated to an internal temperature of 65° C. to 70° C. A 35% aqueous hydrogen peroxide solution (4.13 g, 42.5 mmol, 500 mol %, containing 2.7 g (0.3 L/mol) of water) was added dropwise thereto at an internal temperature of 65° C. to 70° C. over 1 hour, and the mixture was aged for 6 hours while the internal temperature was maintained at 65° C. to 70° C.

Acetonitrile was added to the reaction mixture to make it homogeneous. As a result of analysis by the HPLC external standard method, the target product (5-a) was obtained with a yield of 96%.

Example 9

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, a solution of the compound (4-a) in acetonitrile (86.2 g, purity: 42%, 100 mmol, 100 mol %, containing 50.3 g (0.6 L/mol) of acetonitrile), 10 ml (0.1 L/mol) of water and sodium tungstate dihydrate (1.6 g, 5 mmol, 5 mol %) were added to a reaction flask. The mixture was heated to an internal temperature of 70° C. to 80° C. A 35% aqueous hydrogen peroxide solution (24.3 g, 250 mmol, 250 mol %, containing 15.8 g (0.2 L/mol) of water) was added dropwise thereto at an internal temperature of 70° C. to 80° C. over 1 hour, and the mixture was aged for 5 hours while the internal temperature was maintained at 75° C. to 80° C.

A 20% aqueous sodium sulfite solution (31.5 g, 50 mmol, 50 mol %) was added to the reaction mixture, and the resulting mixture was stirred at an internal temperature of 60° C. to 70° C. for 30 minutes. The obtained mixture was separated into an organic layer and an aqueous layer. To the obtained organic layer was added 50 ml (0.5 L/mol) of water, and the mixture was concentrated under reduced pressure. To the obtained crude product was added 117.8 ml (1.5 L/mol) of isopropanol, and crystals were separated by filtration at room temperature. The thus obtained crystals were washed successively with 12.4 ml of isopropanol (0.2 L/mol) and 10 ml of water (0.1 L/mol). As a result, crystals of a target product (compound 5-a) were obtained with a yield of 95%.

Example 10

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (0.9 g, purity: 100%, 2.5 mmol, 100 mol %), 2 mL (0.8 L/mol) of dimethylformamide, and sodium tungstate dihydrate (41 mg, 0.125 mmol, 5 mol %) were added to a reaction flask. The mixture was heated to an internal temperature of 75° C. to 80° C. A 35% aqueous hydrogen peroxide solution (0.85 g, 8.75 mmol, 300 mol %, containing 0.55 g (0.2 L/mol) of water) was added thereto, and the mixture was aged for 6 hours.

As a result of analysis performed at this point of time, the target product (5-a) was 97% (HPLC area percentage; 230 nm).

Example 11

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (100.1 g, purity: 35%, 100 mmol, 100 mol %, containing 62.5 g (0.8 L/mol) of 2-propanol), 10 ml (0.1 L/mol) of water and ammonium molybdate tetrahydrate (1.23 g, 1 mmol, 1 mol %) were added to a reaction flask. The mixture was heated to an internal temperature of 75° C. to 80° C. A 35% aqueous hydrogen peroxide solution (29.2 g, 300 mmol, 300 mol %, containing 12.8 g (0.12 L/mol) of water) was added dropwise thereto at an internal temperature of 75° C. to 80° C. over 1 hour, and the mixture was aged for 5 hours while the internal temperature was maintained at 75° C. to 80° C. Besides, a 35% aqueous hydrogen peroxide solution (19.5 g, 200 mmol, 200 mol %, containing 19 g of water (0.19 L/mol)) was added dropwise thereto, and the resultant mixture was aged for 5 hours with the internal temperature maintained at 75° C. to 80° C.

The reaction mixture was stirred and cooled to room temperature and the crystals were separated by filtration at room temperature. The obtained crystals were washed successively with 10 ml (0.1 L/mol) of isopropanol and 10 ml (0.1 L/mol) of water. As a result, crystals of the target product (5-a) were obtained with a yield of 93%.

Next, formulation examples of the pest control agent of the present invention using the heterocyclic compound of the present invention produced as described above or an agriculturally acceptable salt thereof will be specifically described. It is noted that types of compounds and additives and blending ratios thereof are not limited to those described herein but can be changed in wide ranges. Besides, in the following description, the term "part(s)" means "part(s) by mass".

Example 12

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (0.90 g, purity: 100%, 2.5 mmol, 100 mol %), acetic acid (2.69 g, 44.8 mmol, 1790 mol %, 1.0 L/mol), and sodium tungstate dihydrate (0.025 g, 0.075 mmol, 3 mol %) were added to a reaction flask. A 30% aqueous hydrogen peroxide solution (0.71 g, 6.25 mmol, 250 mol %, containing 0.50 g of water (0.2 L/mol)) was added dropwise thereto at an internal temperature of 50° C. to 55° C. over 20 minutes. When the resultant mixture was stirred at an internal temperature of 50° C. to 55° C., and aged for 2 hours, crystals were precipitated, and the mixture became a suspension. The resultant was aged for another 2 hours at an internal temperature of 50° C. to 55° C. Acetonitrile was added to the resultant reaction mixture to obtain a homogeneous solution. As a result of analysis by the HPLC external standard method, the yield of the target (5-a) was 90.0%.

Example 13

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (3.05 g, purity: 100%, 8.5 mmol, 100 mol %), acetic acid (17.7 g, 295 mmol, 3470 mol %, 2 L/mol), and sodium tungstate dihydrate (0.084 g, 0.26 mmol, 3 mol %) were added to a reaction flask. A 35% aqueous hydrogen peroxide solution (2.48 g, 25.5 mmol, 300 mol %, containing 1.6 g of water (0.2 L/mol)) was added dropwise thereto at an internal temperature of 25° C. to 30° C. over 1 hour. The resultant mixture was stirred at an internal temperature of 25° C. to 30° C., and aged for 24 hours. Acetonitrile was added to the resultant reaction mixture to obtain a homogeneous solution. As a result of analysis by the HPLC external standard method, the yield of the target (5-a) was 93.0%.

Example 14

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (0.90 g, purity: 100%, 2.5 mmol, 100 mol %), 2.94 g of acetonitrile (1.5 L/mol), sulfuric acid (0.77 g, 7.50 mmol, 300 mol %), and a 35% aqueous hydrogen peroxide solution (0.81 g, 7.12 mmol, 285 mol %, containing 0.57 g of water (0.2 L/mol))

were added to a reaction flask, followed by stirring at 75° C. for aging for 6 hours. Acetonitrile was added to the resultant reaction mixture to dissolve the reaction mixture into a homogeneous solution. As a result of analysis by the HPLC external standard method, the target (5-a) was obtained with a yield of 86%.

Example 15

The reaction and the analysis were performed in the same manner as in Example 14 except that the amount of acetonitrile was changed to 0.5 L/mol, that the amount of sulfuric acid was changed to 50 mol %, and that the aging time was changed to 18 hours. As a result of the analysis, the target (5-a) was obtained with a yield of 90%.

Example 16

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (0.90 g, purity: 100%, 2.5 mmol, 100 mol %), 2.94 g of toluene (1.5 L/mol), sulfuric acid (0.77 g, 7.50 mmol, 300 mol %), and a 30% aqueous hydrogen peroxide solution (0.81 g, 7.12 mmol, 285 mol %, containing 0.57 g of water (0.2 L/mol)) were added to a reaction flask, followed by stirring at 75° C. for aging for 15 hours. Acetonitrile was added to the resultant reaction mixture to dissolve the reaction mixture into a homogeneous solution. As a result of analysis by the HPLC external standard method, the target (5-a) was obtained with a yield of 91%.

Example 17

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

In a flask, the compound (4-a) 8.98 g, purity: 100%, 25.0 mmol, 100 mol %), 29.6 g of acetonitrile (1.5 L/mol), sulfuric acid (7.51 g, 75.0 mmol, 300 mol %), and a 35% aqueous hydrogen peroxide solution (6.92 g, 71.3 mmol, 285 mol %, containing 4.50 g of water (0.18 L/mol)) were mixed in an ice bath. The entire amount of the resultant mixture was filled in a syringe to be transferred at 0.2 mL/min with a syringe pump. The transferred mixture passed through a Teflon tube having an internal diameter of 2.4 mm and a length of 15 m and submerged in an oil bath at 80° C. to be accumulated in another flask. Two hours after starting the transfer, the reaction mixture was collected and analyzed, and it was thus found that the target (5-a) was 90% (HPLC area percentage; 230 nm). The transfer was further continued, and after 4 hours, the reaction solution was collected and analyzed, and it was thus found that the target (5-a) was 95% (HPLC area percentage; 230 nm).

Example 18

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (0.90 g, purity: 100%, 2.5 mmol, 100 mol %), 3.93 g of acetic acid (1.5 L/mol), and a 30% aqueous hydrogen peroxide solution (0.81 g, 7.12 mmol, 285 mol %, containing 0.57 g of water (0.2 L/mol)) were added to a reaction flask, followed by stirring at 50° C. for aging for 12 hours. Acetonitrile was added to the resultant reaction mixture to dissolve the reaction mixture into a homogeneous solution. As a result of analysis by the HPLC external standard method, the target (5-a) was obtained with a yield of 94%.

Example 19

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (0.90 g, purity: 100%, 2.5 mmol, 100 mol %), dichloroacetic acid (5.85 g, 45.4 mmol, 1815 mol %, 1.5 L/mol), and a 35% aqueous hydrogen peroxide solution (0.69 g, 7.13 mmol, 285 mol %, containing 0.45 g of water (0.18 L/mol)) were added to a reaction flask, followed by stirring at an internal temperature of 50° C. to 55° C. for aging for 1 hour. The resultant mixture was homogeneous from the start of the reaction to the end of the reaction. Acetonitrile was added to the reaction mixture. As a result of analysis by the HPLC external standard method, the target (5-a) was obtained with a yield of 88%.

Example 20

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (0.90 g, purity: 100%, 2.5 mmol, 100 mol %), trichloroacetic acid (3.79 g, 23.2 mmol, 929 mol %, 0.93 L/mol), and a 35% aqueous hydrogen peroxide solution (0.69 g, 7.13 mmol, 285 mol %, containing 0.45 g of water (0.18 L/mol)) were added to a reaction flask, followed by stirring at an internal temperature of 50° C. to 55° C. for aging for 1 hour. The resultant mixture was homogeneous from the start of the reaction to the end of the reaction. Acetonitrile was added to the reaction mixture. As a result of analysis by the HPLC external standard method, the target (5-a) was obtained with a yield of 91%.

Example 21

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

In a flask, the compound (4-a) (3.59 g, purity: 100%, 10.0 mmol, 100 mol %), 7.88 g of acetonitrile (1.0 L/mol), trifluoroacetic acid (3.42 g, 30.0 mmol, 300 mol %), and a 35% aqueous hydrogen peroxide solution (2.77 g, 28.5 mmol, 285 mol %, containing 1.80 g of water (0.18 L/mol)) were mixed at room temperature. The resultant mixture was transferred at 0.1 mL/min with a plunger pump. The transferred mixture passed through a tube having an internal diameter of 4 mm and a length of 3.6 mm and submerged in a hot water bath at 90° C. to be accumulated in another flask. Two hours after starting the transfer, the reaction mixture was collected and analyzed, and it was thus found that the target (5-a) was 91% (HPLC area percentage; 230 nm).

Example 22

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

In a reaction flask, the compound (4-a) (0.90 g, purity: 100%, 2.5 mmol, 100 mol %) was dissolved in 3.14 g of acetonitrile (1.6 L/mol), followed by stirring at 50 to 60° C. To the resultant, 2 ml of a 0.6 M aqueous potassium carbonate solution (0.8 L/mol, 48 mol %) and a 35% aqueous hydrogen peroxide solution (1.22 g, 12.5 mmol, 500 mol %, containing 0.79 g of water (0.3 L/mol)) were simultaneously added dropwise over 5 hours, followed by stirring at 60° C. for aging for 1 hour. Acetonitrile was added to the resultant reaction mixture to dissolve the reaction mixture into a homogeneous solution. As a result of analysis by the HPLC external standard method, the target (5-a) was obtained with a yield of 82%.

Example 23

The reaction and the analysis were performed in the same manner as in Example 19 except that the amount of hydrogen peroxide was changed to 350 mol %, that the time of dropwise addition of hydrogen peroxide was changed to 1 hour, and that the potassium carbonate (48 mol %) was changed to sodium bicarbonate (36 mol %). As a result of analysis, the target (5-a) was obtained with a yield of 91%.

Example 24

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

Under a nitrogen stream, the compound (4-a) (0.90 g, purity: 100%, 2.5 mmol, 100 mol %), 2.94 g of acetonitrile (1.5 L/mol), sulfuric acid (0.023 g, 0.225 mmol, 9 mol %) and a 30% aqueous hydrogen peroxide solution (0.81 g, 7.12 mmol, 285 mol %, containing 0.57 g of water (0.2 L/mol)) were added to a reaction flask, followed by stirring at 75° C. for aging for 6 hours.

Thereafter, the resultant reaction mixture was cooled to room temperature, and the pH at this point of time was −0.05.

Under stirring the reaction mixture at room temperature, a 30% aqueous hydrogen peroxide solution (0.61 g, 5.37 mmol, 215 mol %, containing 0.43 g of water (0.17 L/mol)), and a 0.6 M aqueous potassium carbonate solution (3.0 g, 1.80 mmol, 72 mol %) were added thereto, followed by stirring at room temperature for aging for 0.5 hours. The pH at this point of time was 9.31. Acetonitrile was added to the reaction mixture to dissolve the reaction mixture into a homogeneous solution. As a result of analysis by the HPLC external standard method, the target (5-a) was obtained with a yield of 80%.

Example 25

(Step iii)

Production of 3-[(5-difluoromethoxy-1-methyl-3-trifluoromethylpyrazol-4-yl)methylsulfonyl]-4,5-dihydro-5,5-dimethylisoxazole (Compound 5-a)

The reaction formula is the same as that of Example 7.

The compound (4-a) (0.45 g, purity: 100%, 1.25 mmol, 100 mol %), 0.83 g of acetonitrile (0.85 L/mol), 3.19 g of water (2.55 L/mol), and 45% potassium hydrogen persulfate (1.88 g, 1.38 mmol, 110 mol %) were added to a reaction flask, followed by stirring at 80° C. for aging for 3 hours. At this point of time, the target (5-a) was 95.7% (HPLC area percentage; 230 nm).

[Formulation Example 1] Wettable Powder

| | |
|---|---|
| Compound of Formula (2-a) of the present invention | 10 parts |
| Naphthalenesulfonate formalin condensate sodium | 0.5 parts |
| Polyoxyethylene alkyl aryl ether | 0.5 parts |
| Diatomite | 24 parts |
| Clay | 65 parts |

These components were mixed and pulverized to obtain a wettable powder.

Next, effects exhibited by the pest control agent of the present invention will be described with reference to test examples.

[Test Example 1] Insecticidal Activity Test Against *Helicoverpa Armigera*

A wettable powder prepared in accordance with Formulation Example 1 was diluted with water to a concentration of 500 ppm as the active ingredient. A cabbage leaf was dipped in the resultant chemical solution, air-dried, and then put in a plastic cup. Five hatched larvae of *Helicoverpa armigera* were released therein, and the resultant was covered. Thereafter, the resultant was placed in a constant temperature chamber of 25° C., and after 6 days, the number of dead larvae was counted to obtain a corrected mortality rate in accordance with the following equation of Expression 1. The test was performed in duplicate.

[Expression 1]

$$\text{Corrected mortality rate (\%)} = \{(\text{survival rate in untreated plot} - \text{survival rate in treated plot})/\text{survival rate in untreated plot}\} \times 100$$

The compound of formula (2-a) of the present invention exhibited a corrected mortality rate of 75% in this test.

On the other hand, the same test was performed using a di[(pyrazol-3-yl)methyl]disulfide compound (formula A) described in U.S. Pat. No. 3,350,407, and as a result, the corrected mortality rate thereof was 44%. At the same time, the compound (2-a) of the present invention was retested, and exhibited a corrected mortality rate of 89% in this test.

As a result, the compound (2-a) of the present invention exhibited higher control activity than the compound of formula (A).

(A)

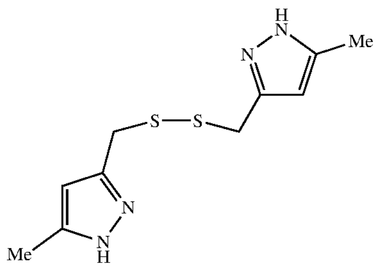

($^1$H-NMR Shift of Compound of Formula A)

$^1$H-NMR value ($CDCl_3$/TMS δ (ppm)): 7.68 (2H, s), 5.96 (2H, s), 3.80 (4H, s), 2.29 (6H, s)

(Melting Point of Comparative Compound)

Melting point: 79.7° C.

The compound of the present invention has pest control activity, and is useful as an active ingredient of a pest control agent.

All publications, patents, and patent applications described herein are hereby fully incorporated by reference in their entirety for the purpose of describing and disclosing the methods described in those publications, patents, and patent applications that may be used in connection with the description herein. To the extent necessary to understand or complete the disclosure of the present invention, all publications, patents, and patent applications described herein are expressly incorporated herein by reference to the same extent as if each were individually incorporated. All publications, patents, and patent applications discussed above and throughout this specification are provided solely for disclosure prior to the filing date of this application.

Any processes and reagents similar or equivalent to those described herein can be employed in the practice of the present invention. Accordingly, the present invention is not to be limited by the foregoing description, but is intended to be defined by the claims and their equivalents. Those equivalents fall within the scope of the present invention as defined by the appended claims.

The invention claimed is:

1. A compound of formula (2), or a mixture thereof:

(2)

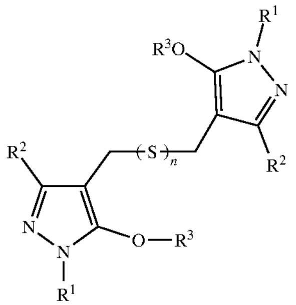

wherein $R^1$, $R^2$ and $R^3$ are each independently a (C1-C6) alkyl optionally substituted with one or more substituents, and n is an integer of 2 or more.

2. The compound or the mixture thereof according to claim 1, wherein $R^1$ is a (C1-C4)alkyl, $R^2$ is a (C1-C4)perfluoroalkyl, $R^3$ is a (C1-C4)alkyl optionally substituted with 1 to 9 fluorine atoms, and n is an integer of 2 to 5.

3. The compound according to claim 1, wherein $R^1$ is methyl, $R^2$ is trifluoromethyl, $R^3$ is a difluoromethyl, and n is 2.

4. A pest control agent comprising, as an active ingredient, the compound or the mixture thereof according to claim 1.

5. A process for producing a compound of formula (4), comprising the following step ii:

(step ii) a step of reacting a compound of formula (2) with a compound of formula (3) to produce a compound of formula (4):

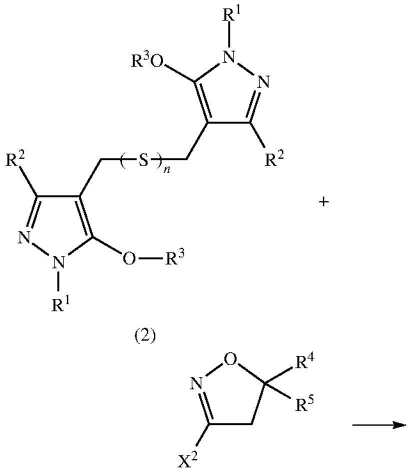

(2)

(3)

-continued

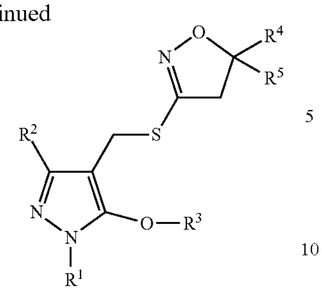

(4)

wherein $R^1$, $R^2$, $R^3$, $R^4$ and $R^5$ are each independently a (C1-C6)alkyl optionally substituted with one or more substituents, $X^2$ is a halogen atom, and n is an integer of 2 or more.

6. The process according to claim 5, wherein the reaction in the step ii is performed using a reducing agent.

7. The process according to claim 6, wherein the reducing agent is an alkali metal hydroxymethanesulfinate or a borohydride compound.

8. The process according to claim 6, wherein the reducing agent is sodium hydroxymethanesulfinate dihydrate or sodium borohydride.

9. The process according to claim 5, wherein the reaction in the step ii is performed in the presence of a base.

10. The process according to claim 9, wherein the base is an alkali metal carbonate or an alkali metal hydroxide.

11. The process according to claim 9, wherein the base is potassium carbonate or sodium hydroxide.

12. The process according to claim 5, wherein the reaction in the step ii is performed using an inorganic sulfur compound.

13. The process according to claim 12, wherein the inorganic sulfur compound is sodium hydrosulfide.

14. The process according to claim 5, wherein $R^1$ is a (C1-C4)alkyl, $R^2$ is a (C1-C4)perfluoroalkyl, $R^3$ is a (C1-C4)alkyl optionally substituted with 1 to 9 fluorine atoms, $R^4$ is a (C1-C4)alkyl, $R^5$ is a (C1-C4)alkyl, n is an integer of 2 to 5, and $X^2$ is a chlorine atom or a bromine atom.

15. The process according to claim 5, wherein $R^1$ is methyl, $R^2$ is trifluoromethyl, $R^3$ is difluoromethyl, $R^4$ is methyl, $R^5$ is methyl, n is 2, and $X^2$ is a chlorine atom or a bromine atom.

16. The process according to claim 5, wherein $X^2$ is a chlorine atom.

17. The process according to claim 5, further comprising the following step i before the step ii:

(step i) a step of producing a compound of formula (2) including reacting a compound of formula (1) with a sulfur compound:

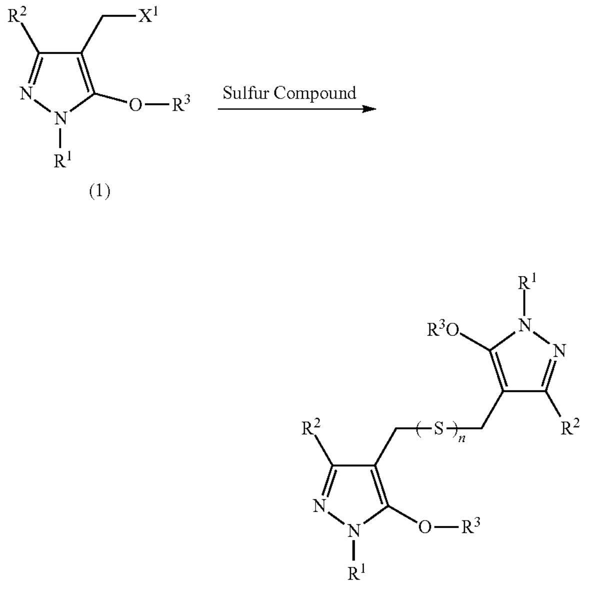

(1)

(2)

wherein $R^1$, $R^2$, and $R^3$ are each independently a (C1-C6)alkyl optionally substituted with one or more substituents, $X^1$ is a halogen atom, and n is an integer of 2 or more.

18. The process according to claim 17, wherein the sulfur compound in the step i is an inorganic sulfur compound and sulfur.

19. The process according to claim 18, wherein the inorganic sulfur compound is sodium sulfide.

20. The process according to claim 17, wherein the sulfur compound in the step i is thiourea.

21. The process according to claim 17, wherein $R^1$ is a (C1-C4)alkyl, $R^2$ is a (C1-C4)perfluoroalkyl, $R^3$ is a (C1-C4)alkyl optionally substituted with 1 to 9 fluorine atoms, n is an integer of 2 to 5, and $X^1$ is a chlorine atom or a bromine atom.

22. The process according to claim 17, wherein $R^1$ is methyl, $R^2$ is trifluoromethyl, $R^3$ is difluoromethyl, n is 2, and $X^1$ is a chlorine atom or a bromine atom.

23. A process for producing a compound of formula (5), comprising:

(step ii) a step of reacting a compound of formula (2) with a compound of formula (3) to produce a compound of formula (4):

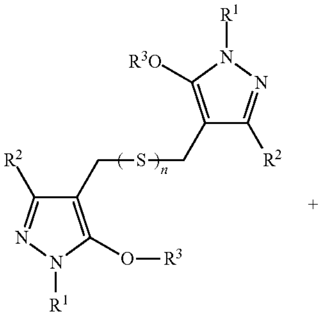

(2)

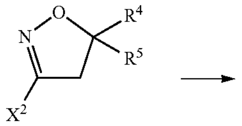

(3)

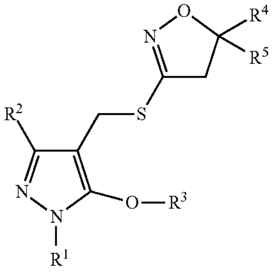

(4)

wherein $R^1$, $R^2$, $R^3$, $R^4$ and $R^5$ are each independently a (C1-C6)alkyl optionally substituted with one or more substituents, $X^2$ is a halogen atom, and n is an integer of 2 or more; and (step iii) a step of reacting the compound of formula (4) with an oxidizing agent to produce the compound of formula (5):

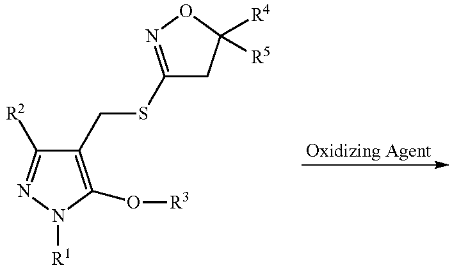

(4)

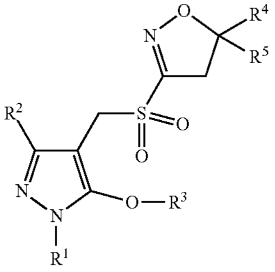

(5)

wherein $R^1$, $R^2$, $R^3$, $R^4$ and $R^5$ are each independently a (C1-C6)alkyl optionally substituted with one or more substituents.

24. A process for producing a compound of formula (2) using a compound of formula (1):

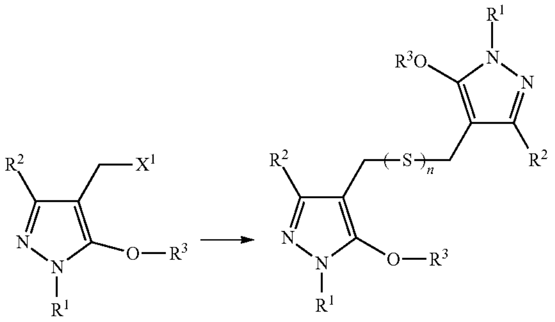

(1) (2)

wherein $R^1$, $R^2$, and $R^3$ are each independently a (C1-C6)alkyl optionally substituted with one or more substituents, $X^1$ is a halogen atom, and n is an integer of 2 or more.

25. A process for producing a compound of formula (2), comprising the following step i:

(step i) a step of producing the compound of formula (2) including reacting a compound of formula (1) with a sulfur compound:

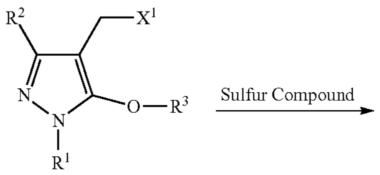

(1)

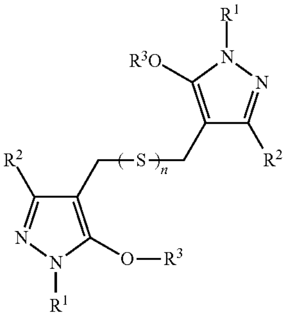

(2)

wherein $R^1$, $R^2$, and $R^3$ are each independently a (C1-C6)alkyl optionally substituted with one or more substituents, $X^1$ is a halogen atom, and n is an integer of 2 or more.

* * * * *